United States Patent
Kang et al.

(10) Patent No.: US 10,085,706 B2
(45) Date of Patent: Oct. 2, 2018

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Dong-Goo Kang, Hwaseong-si (KR); Sunghoon Kang, Suwon-si (KR); Young Hun Sung, Hwaseong-si (KR); Jaemock Yi, Hwaseong-si (KR); Jae Hak Lee, Yongin-si (KR); Seokmin Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 685 days.

(21) Appl. No.: 14/547,559

(22) Filed: Nov. 19, 2014

(65) Prior Publication Data

US 2015/0139394 A1    May 21, 2015

(30) Foreign Application Priority Data

Nov. 19, 2013  (KR) .................. 10-2013-0140964
Oct. 23, 2014  (KR) .................. 10-2014-0144462

(51) Int. Cl.
*A61B 6/00*     (2006.01)
*A61B 6/06*     (2006.01)
*A61B 6/12*     (2006.01)

(52) U.S. Cl.
CPC .............. *A61B 6/5211* (2013.01); *A61B 6/06* (2013.01); *A61B 6/12* (2013.01); *A61B 6/4035* (2013.01); *A61B 6/487* (2013.01); *A61B 6/504* (2013.01); *A61B 6/542* (2013.01); *A61B 6/469* (2013.01)

(58) Field of Classification Search
CPC ......... A61B 6/487; A61B 6/504; A61B 6/542; A61B 6/4035
See application file for complete search history.

(56) References Cited

U.S. PATENT DOCUMENTS

| | | |
|---|---|---|
| 5,278,887 A | 1/1994 | Chiu et al. |
| 2002/0070365 A1 | 6/2002 | Karellas |
| 2005/0089146 A1 | 4/2005 | Toth et al. |

(Continued)

FOREIGN PATENT DOCUMENTS

| | | |
|---|---|---|
| JP | 2007-97977 A | 4/2007 |
| JP | 2007-135658 A | 6/2007 |

(Continued)

OTHER PUBLICATIONS

Communication dated May 31, 2017 issued by the European Patent Office in counterpart European Patent Application No. 14863719.2.

(Continued)

*Primary Examiner* — Dani Fox
(74) *Attorney, Agent, or Firm* — Sughrue Mion, PLLC

(57) ABSTRACT

An X-ray imaging apparatus includes an X-ray source configured to radiate X-rays onto an object region, an X-ray detector configured to detect the radiated X-rays and obtain image frames of the object region based on the detected X-rays, and a filter configured to filter X-rays radiated from the X-ray source such that the X-rays incident on a region of interest (ROI) of the object region have a lower dose than a dose of X-rays incident on a non-ROI of the object region.

49 Claims, 24 Drawing Sheets

(56) References Cited

U.S. PATENT DOCUMENTS

| | | |
|---|---|---|
| 2006/0203966 A1 | 9/2006 | Mollus et al. |
| 2007/0083114 A1 | 4/2007 | Yang et al. |
| 2008/0118023 A1 | 5/2008 | Besson |
| 2011/0261926 A1 | 10/2011 | Hangartner et al. |
| 2012/0057674 A1 | 3/2012 | Zhang |
| 2012/0215095 A1 | 8/2012 | Av-Shalom et al. |
| 2015/0272520 A1* | 10/2015 | Kobayashi ............... A61B 6/06 378/62 |

FOREIGN PATENT DOCUMENTS

| | | |
|---|---|---|
| KR | 10-0687846 B1 | 2/2007 |
| KR | 10-0962787 B1 | 6/2010 |
| KR | 10-2015-0050604 A | 5/2015 |
| WO | 2013132387 A2 | 9/2013 |
| WO | 2014083459 A1 | 6/2014 |
| WO | 2014106783 A1 | 7/2014 |
| WO | 2015019232 A2 | 2/2015 |

OTHER PUBLICATIONS

International Search Report dated Feb. 25, 2015 issued by International Searching Authority in counterpart International Application No. PCT/KR2014/011119.

* cited by examiner

X-RAY IMAGING APPARATUS AND METHOD OF CONTROLLING THE SAME

CROSS-REFERENCE TO RELATED APPLICATIONS

This application claims priority from Korean Patent Application No. 10-2013-0140964, filed on Nov. 19, 2013, and Korean Patent Application No. 10-2014-0144462, filed on Oct. 23, 2014, in the Korean Intellectual Property Office, the disclosures of which are incorporated herein by reference in their entireties.

BACKGROUND

1. Field

Exemplary embodiments relate to an X-ray imaging apparatus that radiates X-rays onto an object and images an inside thereof, and a method of controlling the same.

2. Description of the Related Art

An X-ray imaging apparatus is an apparatus capable of obtaining an internal image of an object by radiating X-rays onto the object and using the X-rays passing through the subject. Since permeability of X-rays differs depending on properties of a substance forming the subject, it is possible to image an internal structure of the object by detecting an intensity or a strength of X-rays passing through the subject. In order to ensure safety of the object when using the X-ray imaging apparatus, reducing a dose of X-rays incident on the object is recognized as an important issue.

SUMMARY

The exemplary embodiments provide an X-ray imaging apparatus capable of decreasing an X-ray dose and minimizing degradation of an image quality of an X-ray image and a field of view (FOV) loss, and a method of controlling the same.

According to an aspect of an exemplary embodiment, there is provided an X-ray imaging apparatus including an X-ray source configured to radiate X-rays onto an object region, an X-ray detector configured to detect the radiated X-rays and obtain image frames of the object region based on the detected X-rays, and a filter configured to filter X-rays radiated from the X-ray source such that the X-rays incident on a region of interest (ROI) of the object region have a lower dose than a dose of X-rays incident on a non-ROI of the object region.

The X-ray imaging apparatus may further include an image processor configured to set the ROI using the plurality of image frames, combine a current image frame, of the image frames, obtained when X-rays of a low dose are incident on the non-ROI with a previous image frame of the plurality of image frames, and perform image restoring on the non-ROI of the current image frame based on the combined image frames.

The image processor may be configured to perform the image restoring by at least one of averaging the current image frame and a previous image frame, summing the current image frame and the previous image frame, or applying motion-compensated spatial filtering or motion-compensated temporal filtering to the current image frame and the previous image frame.

The image processor may be configured to perform the image restoring on the non-ROI and the ROI.

The image processor may be further configured to perform image registration or motion estimation and compensation on the non-ROI on which the image restoring is performed by combining the current image frame with the previous image frame.

The image processor may be further configured to use an image equalization algorithm for matching brightness and contrast of the ROI and the non-ROI of the current image frame on which the image restoring is performed on the non-ROI.

The controller may be configured to set an X-ray imaging mode based on information about the current frame image, information about an imaging mode, or information about a stage.

The controller may be configured to set the X-ray imaging mode as one of a full imaging mode in which X-rays of a uniform dose are radiated onto the ROI and the non-ROI and an ROI mode in which X-rays having a dose lower than a dose of the ROI are radiated onto the non-ROI according to a movement characteristic of the object of interest.

According to a movement characteristic of the object of interest, the controller may be configured to set the X-ray imaging mode as one of a full imaging mode in which the X-rays of a uniform dose are radiated onto the object region and a stationary mode in which a size of the ROI is increased according to the movement of the object of interest and a position of the ROI remains fixed.

According to the movement characteristic of the object of interest, the controller may be configured to set the X-ray imaging mode as one of a dynamic mode in which the ROI is moved according to movement of the object of interest and a stationary mode in which a size of the ROI is increased and a position of the ROI remains fixed.

According to another aspect of an exemplary embodiment, there is provided a method of controlling an X-ray imaging apparatus, including radiating X-rays having a dose lower a dose of X-rays to be radiated onto a region of interest (ROI), onto a non-ROI in an object region, and obtaining image frames of the object region by detecting the radiated X-rays.

The method of controlling an X-ray imaging apparatus may further include radiating X-rays onto the ROI in the object region, detecting the radiated X-rays and obtaining the image frames of the object region based on the detected X-rays, and setting the ROI in the object region using the image frames.

The radiating the X-rays may include filtering of X-rays incident on the non-ROI.

The method of controlling an X-ray imaging apparatus may further include restoring the non-ROI of the image frame by combining a current image frame, obtained when X-rays of the lower dose are incident on the non-ROI, of the image frames, with a previous frame image of the image frames.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Hereinafter, exemplary embodiments of an X-ray imaging apparatus and a method of controlling the same will be described in detail with reference to the accompanying drawings.

Figure 1:
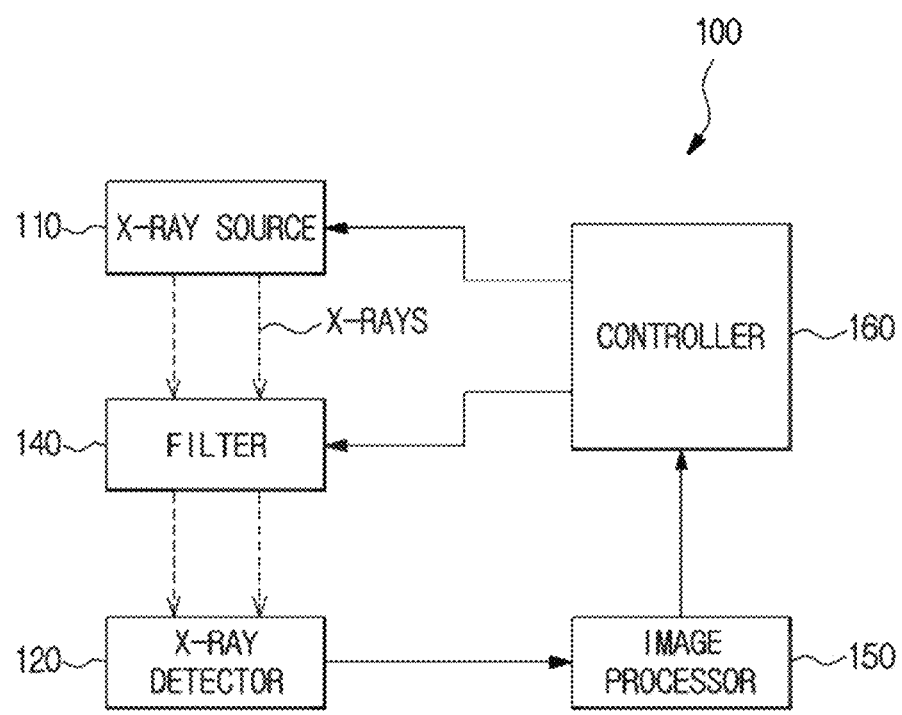
FIG. 1 is a control block diagram illustrating an X-ray imaging apparatus according to an exemplary embodiment.
Figure 2:
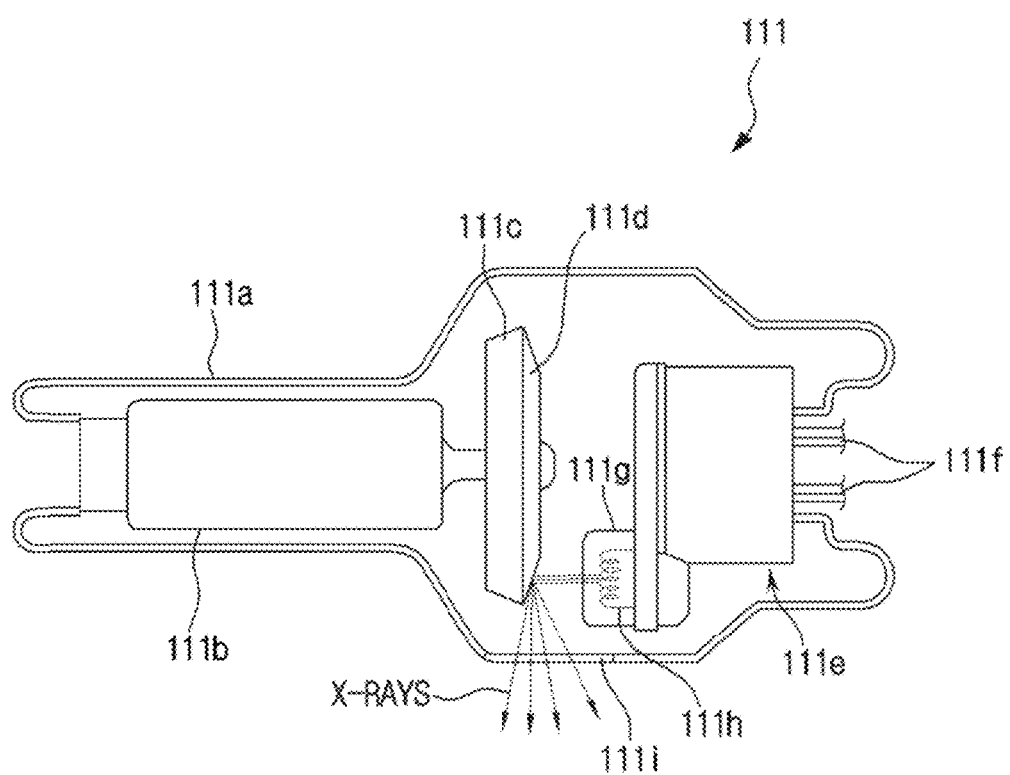
FIG. 2 is a cross sectional view illustrating an internal structure of an X-ray tube included in an X-ray imaging apparatus according to an exemplary embodiment.

FIG. 1 is a control block diagram illustrating an X-ray imaging apparatus according to an exemplary embodiment. FIG. 2 is a cross sectional view illustrating an internal structure of an X-ray tube included in an X-ray imaging apparatus according to an exemplary embodiment.

As illustrated in FIG. 1, an X-ray imaging apparatus 100 includes an X-ray source 110 configured to generate and radiate X-rays, an X-ray detector 120 configured to detect the radiated X-rays and obtain an image frame, a filter 140 configured to filter X-rays radiated from the X-ray source 110, an image processor 150 configured to restore an image quality of an obtained X-ray image, and a controller 160 configured to control the filter 140.

As illustrated in FIG. 2, the X-ray source 110 may include an X-ray tube 111 configured to generate X-rays. An anode 111b and a cathode 111e are provided inside of a glass tube 111a of the X-ray tube 111. The inside of the glass tube 111a is maintained in a high vacuum state and thermoelectrons are generated by heating a filament 111h of the cathode 111e. The filament 111h may be heated by applying a current to an electrical conductor 111f connected to the filament.

The cathode 111e includes the filament 111h and a focusing electrode 111g configured to focus electrons. The focusing electrode 111g is also called a focusing cup. When a high voltage is applied between the anode 111b and the cathode 111e, thermoelectrons are accelerated and collide with a target material 111d of the anode, and thereby X-rays are generated. High-resistance materials such as Cr, Fe, Co, Ni, W, and Mo may be used as the target material 111d of the anode. The generated X-rays are radiated to the outside through a window 111i. A beryllium (Be) thin film and the like may be used as a material of the window 111i.

A voltage applied between the anode 111b and the cathode 111e is referred to as a tube voltage, and a level thereof may be denoted as peak kilo-voltage (kVp). As the tube voltage increases, a rate of thermoelectrons increases. As a result, energy (photon energy) of the X-rays generated by colliding with the target material increases. Also, energy of X-rays may be adjusted by disposing a filter in a radiation direction of the X-rays. A filter configured to filter X-rays of a specific wavelength band is positioned in front of or behind the window 111i, and thereby it is possible to filter X-rays of a specific wavelength band. For example, when a filter made of aluminum or copper is disposed, X-rays of a low-energy band are filtered and energy of radiating X-rays increases.

A current flowing in the X-ray tube 111 is referred to as a tube current and may be denoted as an average value mA. As the tube current increases, an X-ray dose (the number of X-ray photons) increases. Therefore, the energy of X-rays may be controlled by the tube voltage, and the X-ray dose may be controlled by the tube current and an X-ray exposure time.

The X-ray imaging apparatus 100 may generate an X-ray video by applying X-ray fluoroscopy and may be applied to the field of X-ray diagnosis such as angiography or various other types of using the same. The X-ray video may be generated and displayed in real time.

The X-ray imaging apparatus 100 consecutively performs X-ray imaging in order to generate the X-ray video. A method of consecutively performing X-ray imaging includes a continuous exposure method and a pulse exposure method. When the continuous exposure method is applied, a low tube current is continuously supplied to the X-ray tube 111 to continuously generate X-rays. When the pulse exposure method is applied, X-rays are generated by successive short pulses. Accordingly, when the pulse exposure method is applied, it is possible to decrease the X-ray dose and motion blurring. Any of the two methods may be applied to the X-ray imaging apparatus 100. For convenience of description, in the exemplary embodiment to be described below, the pulse exposure method may be applied.

The X-ray source 110 is configured to radiate X-rays onto an object region a plurality of times at predetermined time intervals or at any other time interval. The predetermined time intervals or the other time intervals may be determined according to a pulse rate or a frame rate. For example, the frame rate may be set to 30 frames per second (30 fps), 15 frames per second (15 fps), 7.5 frames per second (7.5 fps), and the like, and the pulse rate may be set to 30 pulses per second (30 pps), 15 pulses per second (15 pps), 7.5 pulses per second (7.5 pps), and the like.

The object refers to an X-ray imaging target, in other words, a target of which an inside may be represented as an X-ray image. The object region is a predetermined region of the object and refers to a region to be imaged as an X-ray image. Accordingly, the object region matches an imaging region (a field of view (FOV)) of the X-ray imaging apparatus 100 or may include the imaging region of the X-ray imaging apparatus 100.

The object region includes at least one of a region of interest (ROI) and a non-ROI. A region other than the ROI in the object region is the non-ROI. The ROI and the non-ROI will be described in detail below.

The X-ray detector 120 detects X-rays and obtains a plurality of image frames of the object region. The image frame refers to each of the plurality of X-ray images obtained according to the frame rate of the X-ray imaging apparatus 100. The X-ray detector 120 may have a 2D array structure including a plurality of pixels. When the detected X-rays are converted into an electrical signal for each pixel, a single X-ray image of the object region is obtained.

The X-ray detector 120 may use various methods to detect X-rays and convert the detected X-rays into an electrical signal. For example, the X-ray detector 120 may use a direct method in which X-rays are directly converted into an electrical signal using a photoconductor such as a-Se, and may use an indirect method in which X-rays are converted into visible light using a scintillator such as a CSI and the visible light is converted into an electrical signal.

The filter 140 filters X-rays radiated from the X-ray source 110 such that X-rays having a dose lower than a dose of the X-rays incident on the ROI are incident on the non-ROI. This feature is implemented to reduce the X-ray dose. Through X-ray filtering, X-rays having a dose greater than a dose of X-rays incident on the non-ROI are applied to the ROI in which much useful information on an inside of the object is included, and X-rays having a dose lower than a dose of X-rays incident on the ROI are applied to the non-ROI in which a small amount of information is included. Since X-rays are also incident on the non-ROI, there is no loss of the imaging region (FOV). A more detailed operation of the filter 140 will be described below.

The image processor 150 may restore an image frame obtained while X-rays having a dose lower than a dose of X-rays incident on the ROI are incident on the non-ROI using at least one previous image frame. When the X-ray dose is small, a signal to noise ratio (SNR) of the X-ray image may decrease. Therefore, the image processor 150 may restore a non-ROI of a current image frame using at least one previous image frame. A detailed description of restoring the non-ROI will be described below.

Also, the image processor 150 analyzes the image frame of the object region and obtains information on the ROI. Analysis of the image frame will be described in detail below.

The controller 160 may control the X-ray source 110 and the filter 140, and for this purpose, receives information on the ROI from the image processor 150, and may determine parameters for controlling the X-ray source 110 and the filter 140 based on the information on the ROI.

Hereinafter, operations of each component of the X-ray imaging apparatus 100 will be described in detail.

Figure 3:
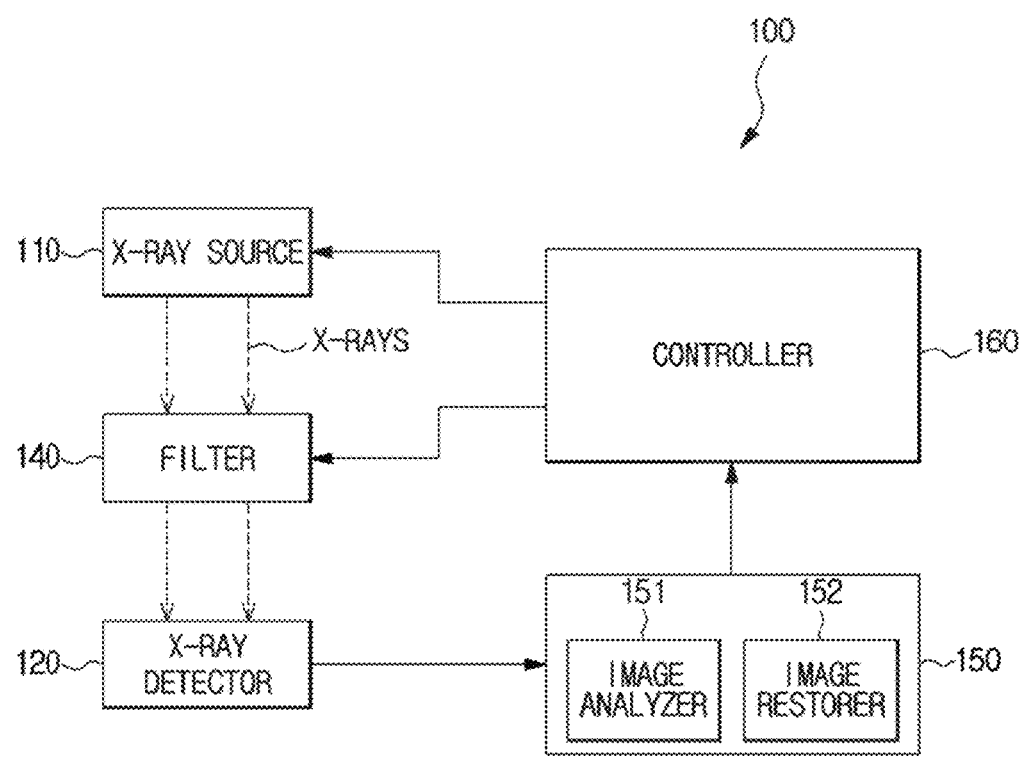
FIG. 3 is a control block diagram illustrating a detailed configuration of an image processor included in an X-ray imaging apparatus according to an exemplary embodiment.
Figure 4:
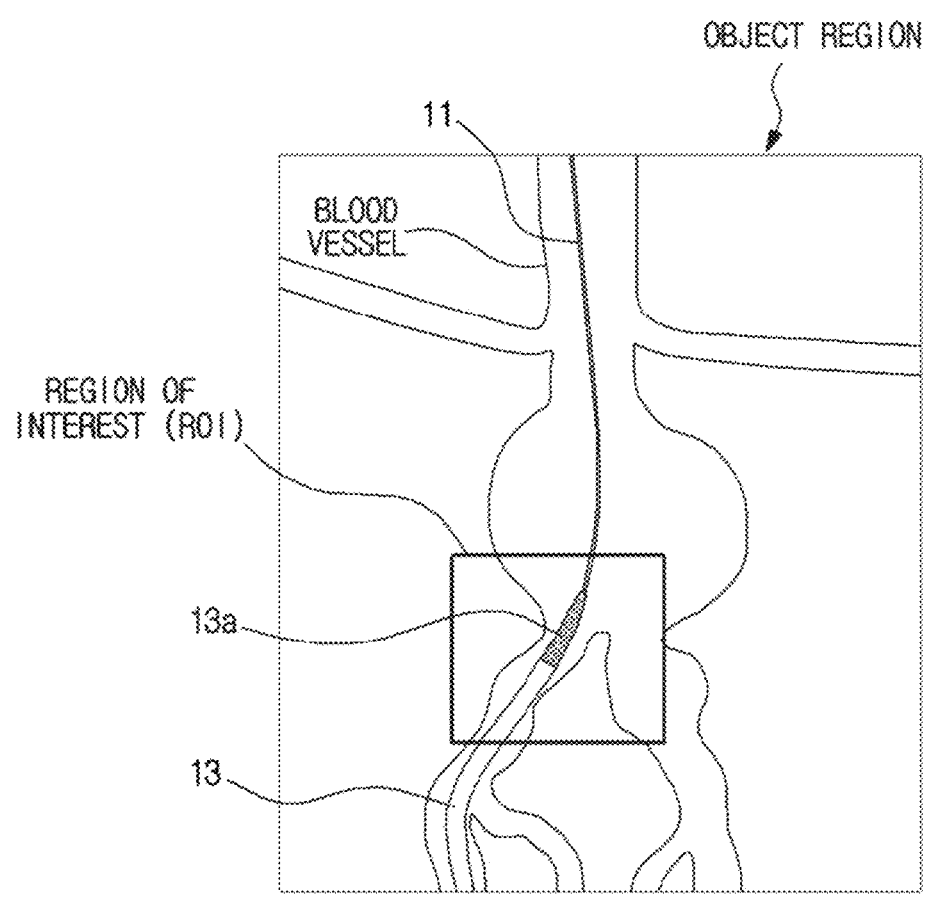
FIG. 4 is a diagram illustrating an exemplary region of interest (ROI) when a stent is inserted into the aorta using angiography.

FIG. 3 is a control block diagram illustrating a detailed configuration of an image processor included in an X-ray imaging apparatus according to an exemplary embodiment. FIG. 4 is a diagram illustrating an exemplary ROI.

As illustrated in FIG. 3, the image processor 150 may include an image analyzer 151 configured to analyze the image frame of the object region and obtain information on the ROI, and an image restorer 152 configured to restore an image quality of a current image frame using previous image frames.

As described above, the X-ray imaging apparatus 100 may obtain the X-ray video of the object region by consecutively performing X-ray imaging. The image frames obtained by the X-ray detector 120 are input to the image processor 150. The image analyzer 151 of the image processor 150 may obtain information on the ROI by analyzing the input image frames.

First, in order to set the ROI, the image analyzer 151 detects an object of interest by performing image processing to perform object recognition on the image frame of the object region. In order to detect the object of interest, image processing may be performed on the current image frame, and image processing may also be performed on the current image frame and at least one previous image frame together. Since there may be a case in which the current image frame has no object of interest, when at least one previous image frame is used together with the current image frame, it is possible to increase detection performance of the object of interest.

In order to detect the object of interest, characteristics of the object of interest are stored in advance, and an object corresponding to the pre-stored characteristic may be detected from the image frame of the object region. Among characteristics of the object of interest, for example, a shape, an X-ray absorption characteristic, and a movement characteristic of the object of interest that can be detected from the X-ray image may be stored in advance.

The object of interest refers to an object that a user continuously watches while X-ray imaging is performed and may be an instrument used for the objector an operation region. If the X-ray imaging apparatus 100 is used for, for example, angiography, when an instrument such as a guide wire, a catheter, a needle, a balloon, or a stent is inserted into a blood vessel, careful observation of the instrument may be needed. Therefore, the instrument is set as the object of interest and information on a characteristic thereof may be stored in advance. Also, when the operation region is set as the object of interest, a region of stenosis or aneurysm, or a cancerous region may be set as the object of interest.

In addition to detection of the object of interest using the pre-stored characteristic of the object of interest as described above, it is possible to detect the object of interest using a marker attached to the object of interest. The marker that can be easily identified in the X-ray image may be used. The image processor 150 may detect the marker instead of the object of interest and therefore detection performance may be increased. The marker may have a characteristic of radiopacity such that the marker can be identified in the X-ray image, and a material thereof may include at least one selected from the group consisting of stainless steel, steel, gold, platinum, and lead.

When the object of interest is detected, the image analyzer 151 sets a predetermined region including the detected object of interest as the ROI. A position and a size of the ROI may be determined in consideration of a position and a size of the object of interest or a movement characteristic of the object of interest. Uncertainty included in the movement characteristic of the object of interest may also be considered.

As an example, when movement of the object of interest is large or the movement characteristic of the object of interest is difficult to predict and therefore uncertainty increases, the image analyzer 151 may set the size of the ROI to be large.

Hereinafter, a specific example of setting the ROI will be described with reference to FIG. 4.

FIG. 4 exemplifies a case in which a stent is inserted into a blood vessel using angiography. A stent 13*a* is inserted into the blood vessel in order to prevent obstruction of the blood vessel and the like, and has a mesh shape. The stent 13*a* is folded and installed at an end of a stent device 13 having a long tube shape, is introduced into the blood vessel, and is spread at a desired position in a mesh shape.

As illustrated in FIG. 4, in order to insert the stent device 13 into the blood vessel of the object region, a guide wire 11 is inserted first. The stent device 13 is inserted into the blood vessel along the guide wire 11. When the stent device 13 is inserted, the stent device 13, and specifically, the stent 13*a* of a tip, may be the object of interest, and a predetermined region including the stent 13*a* may be the ROI.

When the guide wire 11 is inserted, the guide wire 11 or the tip of the guide wire 11 may be the object of interest. While a catheter is inserted in order to inject a contrast agent into the blood vessel, the catheter or a tip of the catheter may be the object of interest.

Meanwhile, the image analyzer 151 may use information input from the outside to detect the object of interest. For example, when information on a kind of the instrument, a kind of the operation, the operation region, injection of the contrast agent, and the like is input, it is possible to detect the object of interest from the image frame based on the input information.

As an example, when information is input indicating that an operation to be performed is an aortic stenting procedure and an instrument to be inserted is a stent device, the image analyzer 151 detects a stent inside the aorta from the image frame of the object region using the pre-stored information on the characteristic of the stent.

The image analyzer 151 may determine the movement characteristic of the object of interest while tracking the detected object of interest. Detecting and tracking the object of interest, and obtaining the information on the ROI, may be performed in real time according to the frame rate of image frames input to the image analyzer 151. According to an exemplary embodiment, obtaining the information on the ROI includes detecting and tracking the object of interest, and setting the ROI based on the result thereof.

The movement characteristic of the object of interest includes information on a position, a movement size, a movement direction, and the like of the object of interest. The movement size may include a speed, but the movement of the object of interest may have no constant pattern. Therefore, the movement size may include various pieces of information indicating a degree of movement in addition to the speed.

The ROI is a predetermined region including the object of interest and is defined by the object of interest. Therefore, the movement characteristic of the ROI may be determined by the movement characteristic of the object of interest.

The image analyzer 151 may estimate periodic movement such as respiration or a heartbeat of a patient and use the movement to set the ROI. For example, there is a case in which the object of interest such as the stent or the catheter may not move on its own but may be moved due to movement of the patient. In this case, since the object of interest moves according to a movement pattern of the patient, the movement of the patient may be predicted and the ROI may be reset using the predicted movement. Specifically, it is possible to reset the ROI such that the ROI is set by detecting the object of interest, and a position or a size of the ROI is compensated for by using a movement amount or a movement direction according to the periodic movement pattern of the patient.

Figure 5:
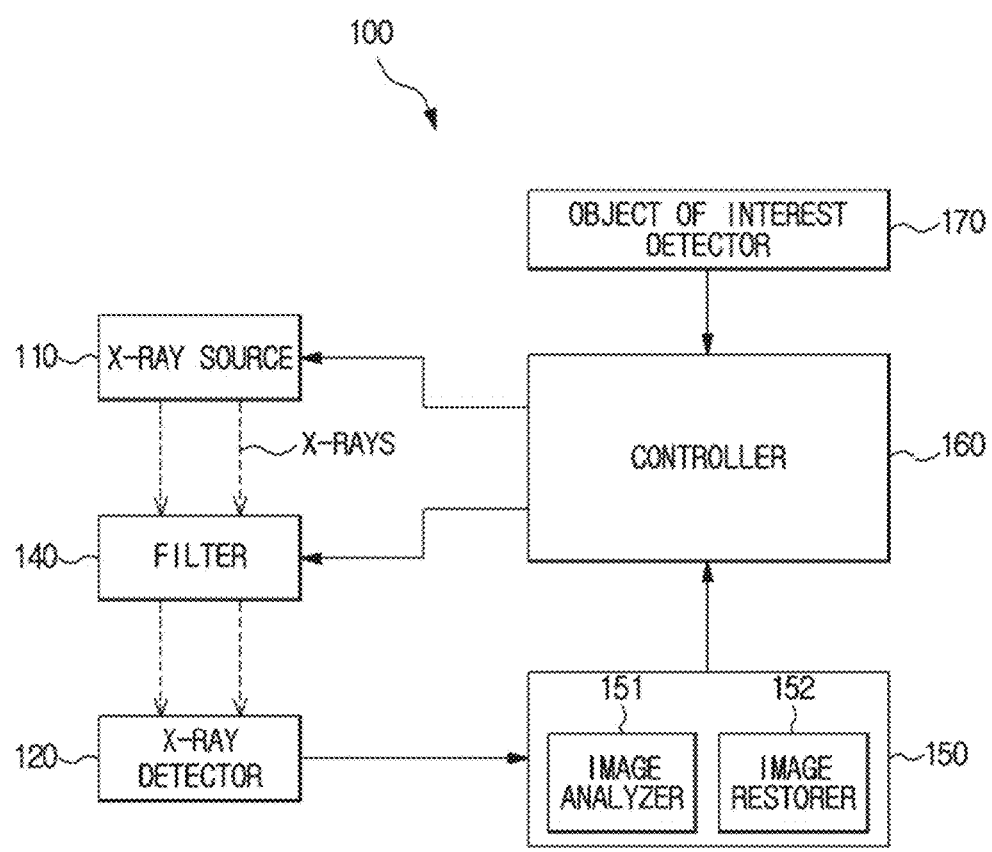
FIG. 5 is a control block diagram illustrating an X-ray imaging apparatus that further includes an object of region detecting unit.

FIG. 5 is a control block diagram illustrating an X-ray imaging apparatus that further includes an object of interest detecting unit.

In the above-described exemplary embodiment, when the object of interest is detected and the ROI is set by using image processing of the X-ray image, a separate sensor capable of estimating position information according to the movement of the object of interest may be used in order to set the ROI. For this purpose, the X-ray imaging apparatus 100 may further include an object of interest detector 170 configured to detect the object of interest as illustrated in FIG. 5.

For example, when a variable magnetic field is applied to a predetermined region including the object of interest and a coil is attached to the object of interest, a voltage applied to the coil is changed according to the movement of the object of interest. Therefore, the voltage applied to the coil is measured, and a position and a movement direction of the coil may be estimated based on the measured voltage. The position and the movement direction of the coil may be treated as a position and a direction of the object of interest. In this case, the object of interest detector 170 may include a magnetic field applying device configured to apply a magnetic field and a voltage sensor configured to measure a voltage.

Also, when the optically recognizable marker is attached to the object of interest and the marker is recognized using an optical sensor, it is possible to estimate the position and the movement direction of the object of interest. In this case, the object of interest detector 170 may include the optical sensor capable of recognizing the marker.

The voltage sensor or the optical sensor may be mounted in any position in which the voltage applied to the coil attached to the object of interest or the marker attached to the object of interest can be recognized. Mounting positions of the sensors are not limited in the exemplary embodiments of the X-ray imaging apparatus 100.

Using the voltage measuring sensor or the optical sensor for detecting the object of interest is only an example. In addition to this method, it is possible to detect the object of interest using various other sensing methods.

When the object of interest is detected using the separate sensor as described above, even if the object of interest is positioned outside an X-ray radiation range, it is possible to detect the object of interest. When the object of interest outside the X-ray radiation range is detected, in order to rapidly move an ROI filter 141 (refer to FIG. 7A) before the object of interest is shown in the X-ray image, the controller 160 may warm up (e.g., supply power to or turn on) a filter driver 143 and move the ROI filter 141 in advance by estimating a movement speed and a movement direction of the object of interest.

The exemplary embodiment of the X-ray imaging apparatus 100 may be configured to perform a combination of two or more methods described above for detecting the object of interest. By using a combination of two or more methods, it may be possible to increase accuracy of detection.

The information on the ROI obtained by the image analyzer 151, and specifically, information on the position, the size, or the movement characteristic of the ROI, is transmitted to the controller 160 and used to control the filter 140.

The image analyzer 151 may also obtain information on image characteristics represented in the image frame, such as noise and contrast, in addition to the information on the ROI. These characteristics may be transmitted to the controller 160 and used to control X-ray imaging conditions.

Figure 6:
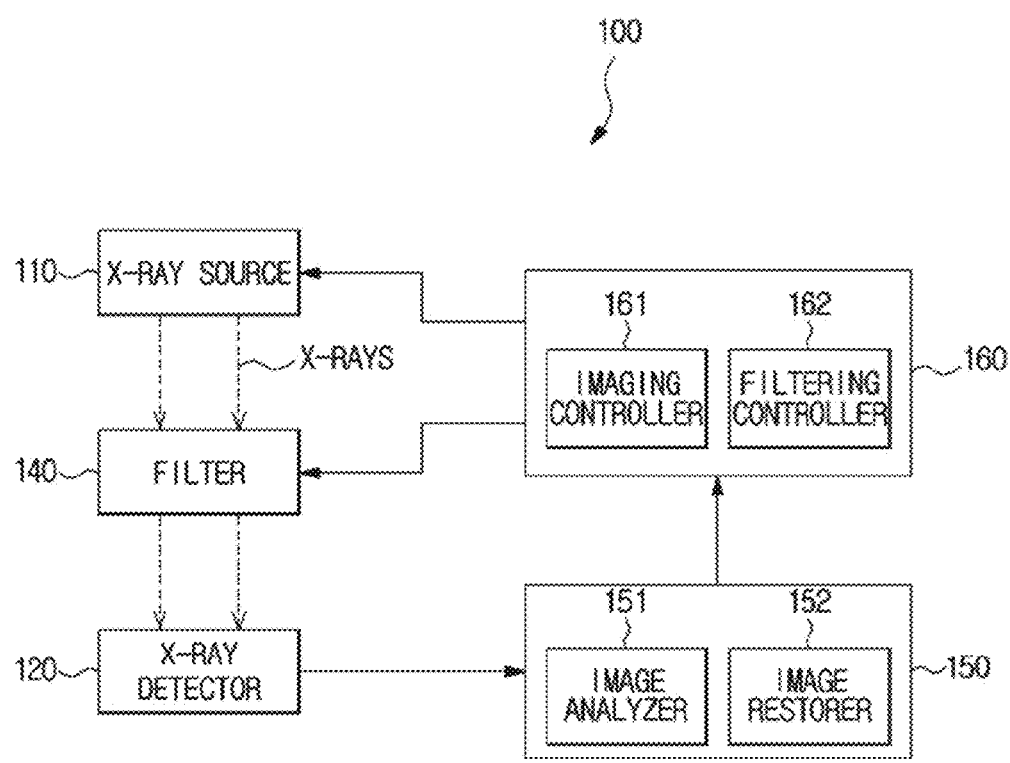
FIG. 6 is a control block diagram illustrating a detailed configuration of a control unit included in an X-ray imaging apparatus according to an exemplary embodiment.

FIG. 6 is a control block diagram illustrating a detailed configuration of a control unit included in an X-ray imaging apparatus according to an exemplary embodiment.

As illustrated in FIG. 6, the controller 160 of the X-ray imaging apparatus 100 includes an imaging controller 161 configured to control X-ray imaging parameters and a filtering controller 162 configured to control the filter 140.

The imaging controller 161 controls various imaging parameters applied to X-ray imaging. The imaging parameter is also called an exposure parameter. Automatically controlling the imaging parameters in the X-ray imaging apparatus 100 is called auto exposure control.

The imaging parameters may be at least one selected from the group including the tube voltage, the tube current, the exposure time, the kind of the filter, the imaging region (FOV), the frame rate, the pulse rate, and the kind of the target material.

The imaging parameter may be determined based on the image frame of the object region and may also be determined based on prior information input before X-ray imaging begins. Hereinafter, an exemplary embodiment of the former case will be described in detail.

The imaging controller 161 may determine the imaging parameter based on an analysis result of the image analyzer 151. For example, when the image analyzer 151 analyzes the image frame and determines characteristics such as a thickness or a density of the subject, the imaging controller 161 may determine imaging parameters such as the tube voltage, the tube current, the exposure time, the kind of the filter, and the kind of the target material, which match the characteristics of the subject, based on the determination result.

Also, the imaging controller 161 may also determine the imaging parameter based on the information on the ROI obtained by the image analyzer 151. According to an exemplary embodiment, the imaging controller 161 determines the imaging parameters such as the frame rate, the tube current, and a dose per frame according to the movement size of the object of interest or characteristics of the image represented in the ROI, and may individually or jointly control the imaging parameters.

For example, when the movement size of the object of interest is large, the imaging controller 161 increases the frame rate and obtains information on the movement of the object of interest to a greater extent, and when the movement size of the object of interest is small, the imaging controller 161 decreases the frame rate and reduces X-ray exposure to the subject.

Also, the imaging controller 161 may control a dose per frame according to a noise level of the ROI. For example, when the noise level of the ROI is greater than a predetermined reference value, the dose per frame is increased to decrease the noise level, thereby making the ROI to be shown more clearly. When the noise level of the ROI is less than the predetermined reference value, the dose per frame is decreased, thereby reducing X-ray exposure to the subject.

The filtering controller 162 controls the filter 140 based on the information on the ROI obtained by the image analyzer 151. In order to describe operations of the filtering controller 162, a configuration of the filter 140 will be described first with reference to FIG. 6.

Figure 7A:
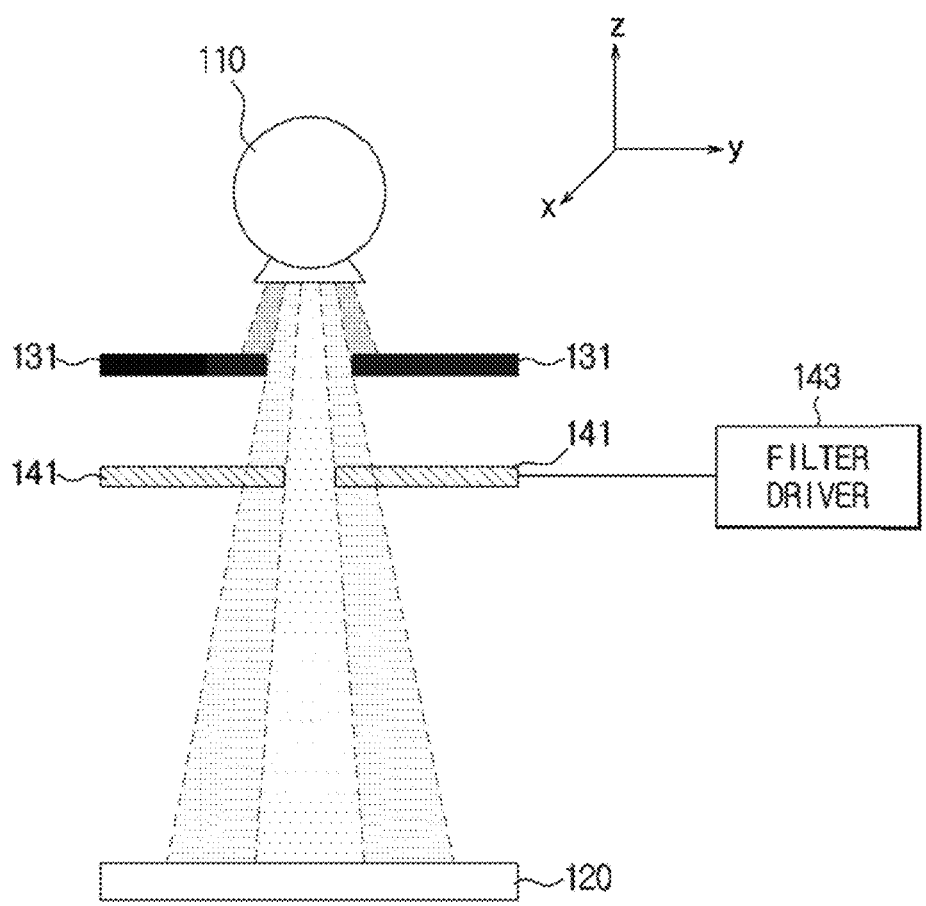
FIG. 7A is a cross sectional side view of an ROI filter included in a filtering unit of an X-ray imaging apparatus according to an exemplary embodiment.
Figure 7B:
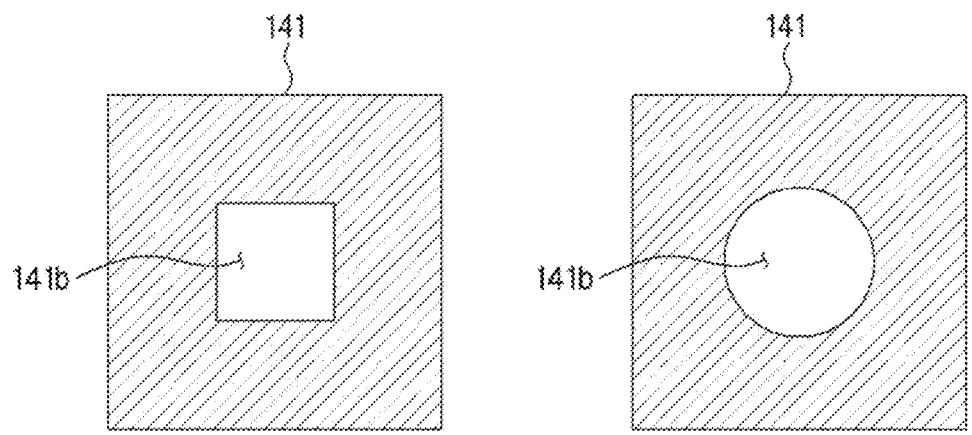
FIG. 7B is a plan view of an exemplary ROI filter.

FIG. 7A is a cross sectional side view of an ROI filter included in a filtering unit. FIG. 7B is a plan view of an exemplary ROI filter.

As illustrated in FIG. 7A, the filter 140 includes an ROI filter 141 and a filter driver 143 configured to move the ROI filter 141. The filter driver 143 may include a mechanical structure such as a motor configured to generate power, a gear configured to deliver the generated power to the ROI filter 141, and the like.

The ROI filter 141 may move on an xy plane or along a z axis by the filter driver 143. Moving on the xy plane is performed such that the ROI filter 141 corresponds to the position of the non-ROI. Moving along the z axis is performed such that the ROI filter 141 corresponds to the size of the ROI.

A collimator 131 may be disposed in an X-ray radiation direction corresponding to a front of the X-ray source 110. The collimator 131 is made of a material that absorbs or blocks X-rays such as lead or tungsten, adjusts a range of the imaging region (FOV) corresponding to an X-ray radiation region of the X-ray source 110, and reduces X-ray scattering.

The ROI filter 141 is positioned between the collimator 131 and the X-ray detector 120, and may filter X-rays radiated from the X-ray source 110. The ROI filter 141 may be made of a material that reduces X-rays. While passing through the ROI filter 141, X-rays decrease and a dose thereof decreases. Therefore, when the ROI filter 141 is positioned at a position corresponding to the non-ROI among the object region, X-rays having a dose lower than a dose of X-rays incident on the ROI may be incident on the non-ROI.

In general, since the ROI is surrounded by the non-ROI, the ROI filter 141 may have an empty center therein, that is, a ring shape in which an opening 141b is formed at a center, as illustrated in FIG. 7B.

The shape of the ROI filter 141 may have a ring shape in which the opening 141b is a polygon such as a rectangular ring as illustrated on the left in FIG. 7B or may have a ring shape in which the opening 141b is a circle as illustrated on the right in FIG. 7B, but the shape of the ROI filter 141 is not limited thereto. The ROI filter 141 may have various shapes according to the characteristic of the ROI, a relation between the ROI and the non-ROI, and the like.

Based on the above-described configuration of the filter 140, operations of the filtering controller 162 will be described. The filtering controller 162 generates a control signal for moving the ROI filter 141 based on the information on the ROI, transmits the generated control signal to the filter driver 143, and may move the ROI filter 141 to a position corresponding to the non-ROI.

As a specific example, the filtering controller 162 may control movement of the ROI filter 141 on the xy plane such that the opening 141b of the ROI filter 141 is positioned at a position corresponding to the ROI, and control movement of the ROI filter 141 along the z axis such that the opening 141b of the ROI filter 141 corresponds to the size of the ROI.

The filtering controller 162 may control the position of the ROI filter 141, and may also control a kind or a thickness of the ROI filter 141. Hereinafter, operations of the filtering controller 162 configured to control the kind or the thickness of the ROI filter 141 will be described with reference to FIG. 8.

Figure 8:
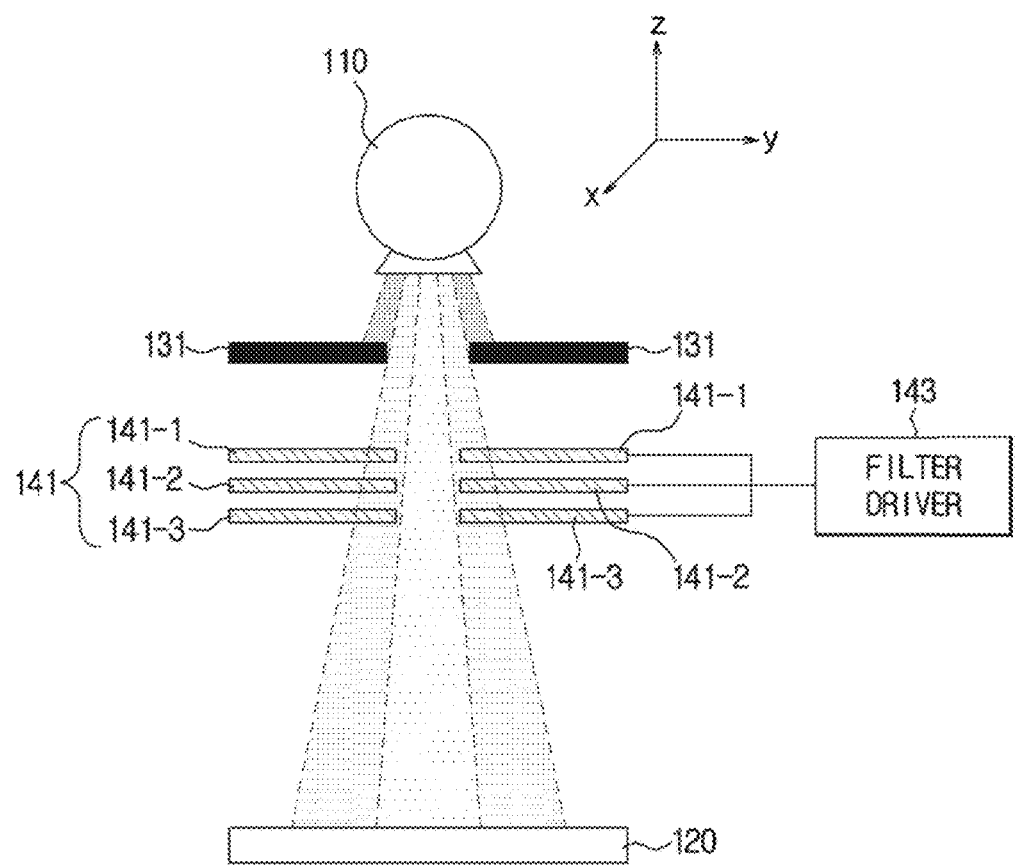
FIG. 8 is a cross sectional view of a filtering unit including a plurality of ROI filters.

FIG. 8 is a cross sectional view of a filtering unit including a plurality of ROI filters.

As illustrated in FIG. 8, the ROI filter 141 may include a plurality of filter layers that are independently movable on the xy plane or along the z axis. The filter layers include a first ROI filter 141-1, a second ROI filter 141-2, and a third ROI filter 141-3.

The first ROI filter 141-1, the second ROI filter 141-2, and the third ROI filter 141-3 may have the same kind but different thicknesses of the filtration material, different kinds and different thicknesses of the filtration material, the same thickness but different kinds of the filtration material, or the same kind and the same thickness of the filtration material.

The filtering controller 162 may determine a difference between X-ray doses to be incident on the ROI and the non-ROI based on the image characteristics of the ROI and the non-ROI such as noise, motion, and contrast, and may variably control the kind or the thickness of the ROI filter according to the determined dose difference.

As an example, the filtering controller 162 may use a combination of the first ROI filter 141-1, the second ROI filter 141-2, and the third ROI filter 141-3. First, based on the image characteristics of the ROI and the non-ROI, a difference between X-ray doses to be incident on the ROI and the non-ROI is determined. A combination of the ROI filters 141-1, 141-2, and 141-3 that enables X-rays to be incident is determined according to the determined dose.

For example, when it is determined that the second ROI filter 141-2 and the third ROI filter 141-3 are to be used, the filtering controller 162 controls the second ROI filter 141-2 and the third ROI filter 141-3 to be positioned at a position in which X-rays radiated from the X-ray source 110 or passed through the collimator 131 may be filtered, and excludes the first ROI filter 141-1 from the filtering position. The filtering controller 162 may move the ROI filter 141 along the z axis or on the xy plane to control the position thereof.

As the ROI filter 141 approaches the X-ray source 110 or the collimator 131, a width of X-rays passing through the opening 141b of the ROI filter 141 decreases. Therefore, in order to increase the ROI by reducing a filtering region, the ROI filter 141 is moved along the z axis toward the X-ray source 110 or the collimator 131. In order to decrease the ROI by increasing the filtering region, the ROI filter 141 is moved along the z axis away from the X-ray source 110 or the collimator 131.

Figure 9A:
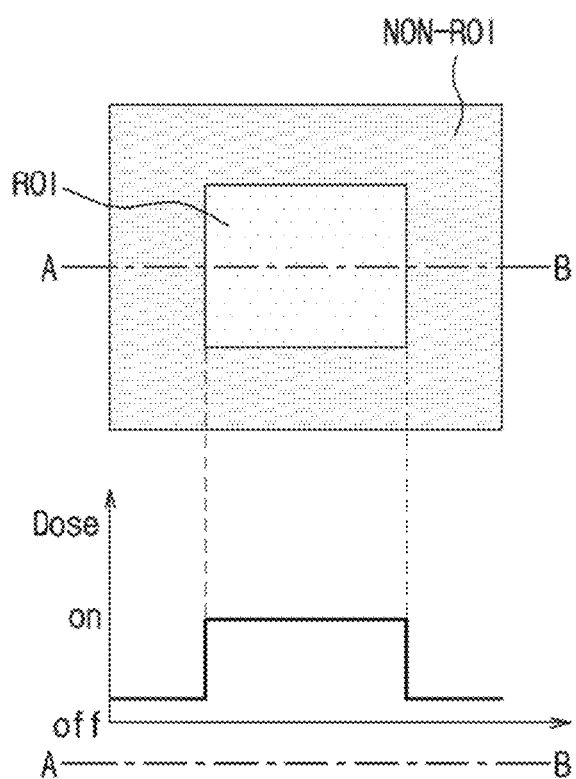
FIGS. 9A and 9B are diagrams schematically illustrating an X-ray dose incident on an ROI and a non-ROI.
Figure 9B:
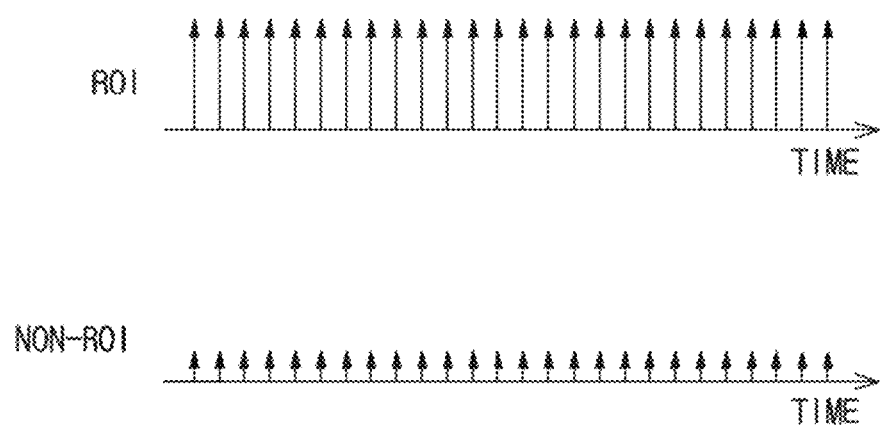

FIGS. 9A and 9B are diagrams schematically illustrating an X-ray dose incident on an ROI and a non-ROI.

FIG. 9A illustrates the X-ray dose incident on an arbitrary straight line AB which crosses the ROI and the non-ROI. When the filtering controller 162 moves the ROI filter 141 to a position corresponding to the non-ROI, as illustrated in FIG. 9A, X-rays having a dose lower than a dose of X-rays incident on the ROI are incident on the non-ROI. Since X-rays are also incident on the non-ROI, though in a small amount, it is possible to obtain information on a full imaging region.

As described above, the X-ray imaging apparatus 100 may obtain the video by consecutively performing X-ray imaging. As long as the ROI is in the object region, a difference between X-ray doses to be incident on the ROI and the non-ROI may be maintained as illustrated in FIG. 8B. For example, the X-ray dose to be incident on the non-ROI may be ⅕, ⅒, or 1/20 or less of the X-ray dose to be incident on the ROI.

Figure 10A:
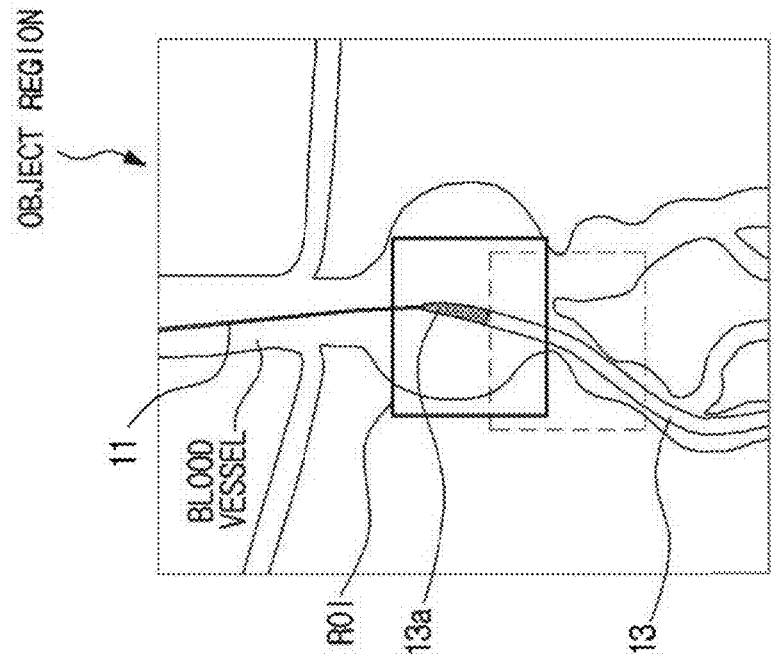
FIG. 10A is a diagram illustrating movement of an ROI according to movement of an object of interest.
Figure 10A:
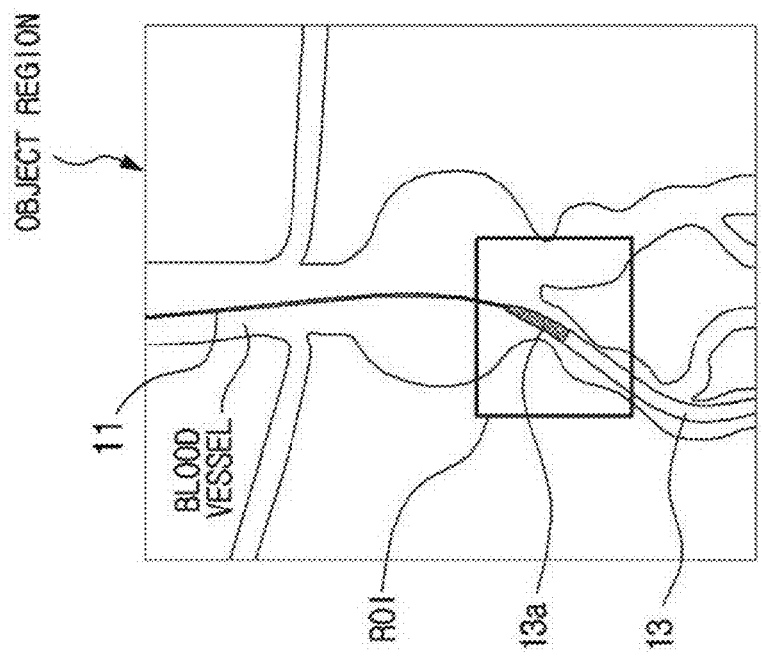
Figure 10B:
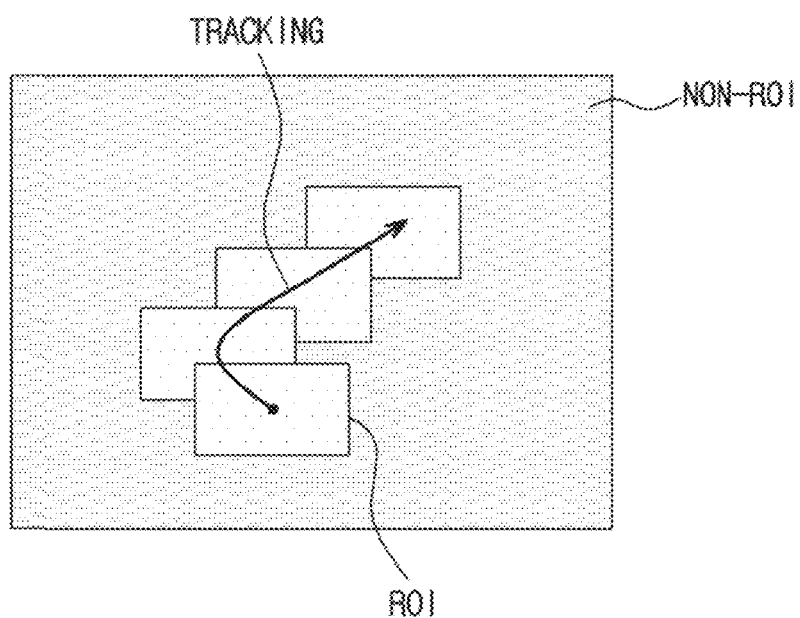
FIG. 10B is a diagram schematically illustrating an operation of tracking a moving ROI.

FIG. 10A is a diagram illustrating movement of an ROI according to movement of an object of interest. FIG. 10B is a diagram schematically illustrating an operation of tracking a moving ROI.

The X-ray video may represent a movement in the object region. When an object of the movement is the object of interest, the ROI may move according to the movement of the object of interest. As an example, as illustrated in FIG. 10A, when a stenting procedure of inserting the stent device 13 into the blood vessel is performed, the stent 13a serving as the object of interest moves to a target position inside the blood vessel and the ROI also moves according to the movement of the stent 13a.

It was described above that the image analyzer 151 may detect and track the object of interest in real time. As illustrated in FIG. 10B, when the ROI moves, the image analyzer 151 tracks the movement of the ROI in real time, and the filtering controller 162 performs control such that the ROI filter 141 is synchronized with the movement of the ROI and moves along therewith.

The image analyzer 151 may fail to detect the object of interest or may detect the object of interest but with a low reliability. For example, reliability of detection may be obtained by various algorithms of calculating reliability of an object recognition result. When a reliability value is less than a predetermined reference value, it may be determined that the detection result of the object of interest is unreliable. When detection of the object of interest fails or reliability thereof is less than the predetermined reference value, the image analyzer 151 does not reset the ROI and may maintain the previous ROI without change.

Figure 11:
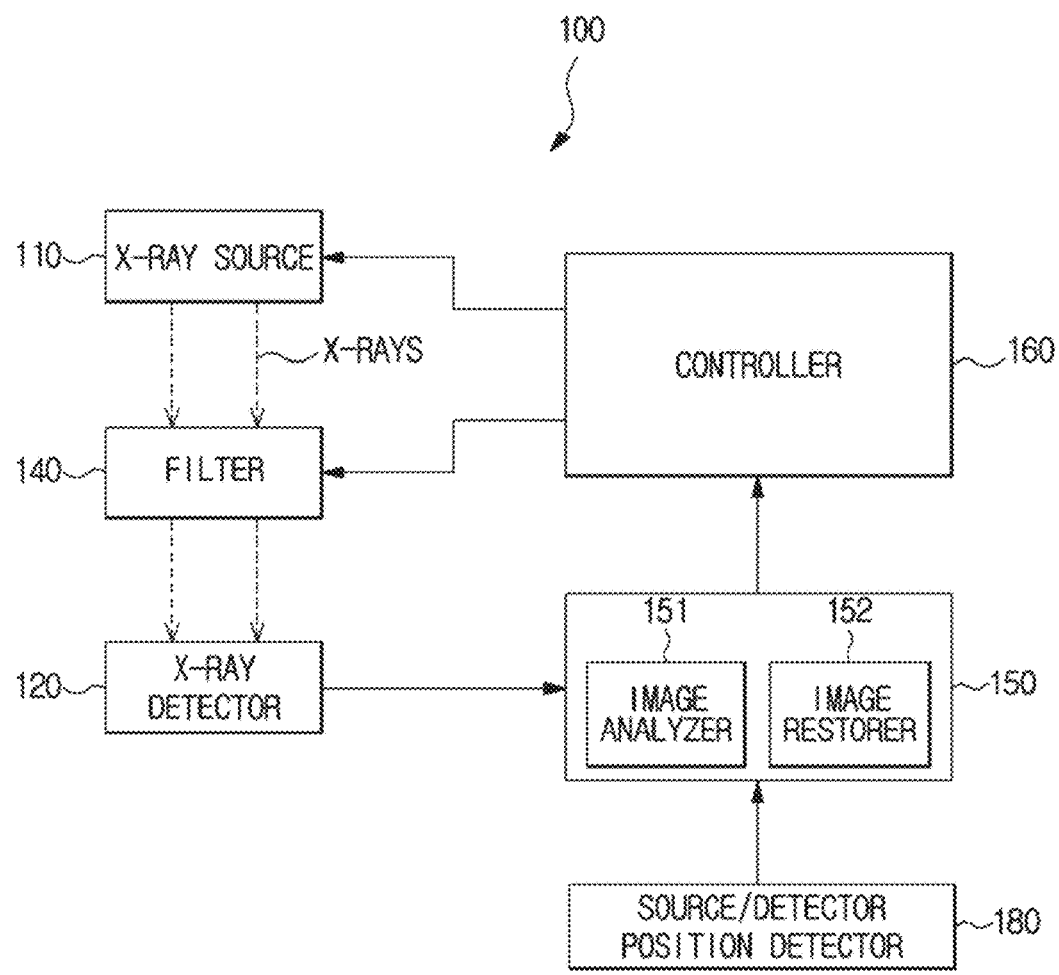
FIG. 11 is a control block diagram illustrating an X-ray imaging apparatus that further includes a source/detector position detecting unit.

FIG. 11 is a control block diagram illustrating an X-ray imaging apparatus that further includes a source/detector position detecting unit.

When X-ray imaging is performed, a position of the X-ray source 110 or the X-ray detector 120 may be changed. The user may manually move the X-ray source 110 or the X-ray detector 120. The X-ray source 110 or the X-ray detector 120 may automatically move. Even when the object of interest is not moved, when the X-ray source 110 or the X-ray detector 120 moves, a relative position between the object of interest and the X-ray source 110 or the X-ray detector 120 may be changed. In this case, a similarity between the previous image frame and the current image frame may decrease, and even when the image analyzer 151 detects and tracks the object of interest in real time, performance or reliability of detection of the object of interest may decrease. Therefore, when the X-ray source 110 or the X-ray detector 120 is moved, the image analyzer 151 may detect the object of interest and reset the ROI by reflecting a change in the position of the X-ray source 110 or the X-ray detector 120. Specifically, the image analyzer 151 may estimate a relative position change with the object of interest according to the position change of the X-ray source 110 or the X-ray detector 120, reflect the relative position change when the object of interest is detected, and prevent a decrease in performance or reliability of detection.

For this purpose, the X-ray imaging apparatus 100 may further include a source/detector position detector 180, e.g., detector, capable of detecting a change in the position of the X-ray source 110 or the X-ray detector 120, as illustrated in FIG. 11. The source/detector position detector 180 may be implemented as a position sensor to obtain position information of the X-ray source 110 or the X-ray detector 120, and when the X-ray source 110 or the X-ray detector 120 is automatically movable by a driving unit such as a motor, may be implemented as a sensor configured to measure a driving amount of the driving unit and obtain information on a movement amount or a movement direction of the X-ray source 110 or the X-ray detector 120.

Also, when the X-ray source 110 or the X-ray detector 120 is automatically moved under control of the controller 160, the source/detector position detector 180 may not be provided, and the information on the movement amount or the movement direction of the X-ray source 110 or the X-ray detector 120 may be obtained from the controller 160.

A configuration or a method of obtaining the information on the position change of the X-ray source 110 or the X-ray detector 120 is not limited in any particular way according to the exemplary embodiments of the X-ray imaging apparatus 100. In addition to the above-described example, the information on the position change of the X-ray source 110 or the X-ray detector 120 may be obtained using various methods.

The ROI moves together with the movement of the object of interest in the example in FIG. 10B. However, according to another example, the size of the ROI may be changed according to the movement of the object of interest. For example, the image analyzer 151 fixes the position of the ROI when the object of interest moves, and may increase a size thereof to include the moved object of interest. Therefore, the size of the ROI is changed according to the movement size of the object of interest.

Also, as will be described below, when the movement size of the object of interest is small, the position of the ROI may be fixed and only a size thereof may be increased.

The X-ray imaging apparatus 100 may perform road mapping. When road mapping is performed, the X-ray dose may also be adjusted through detecting and tracking the ROI.

Figure 12:
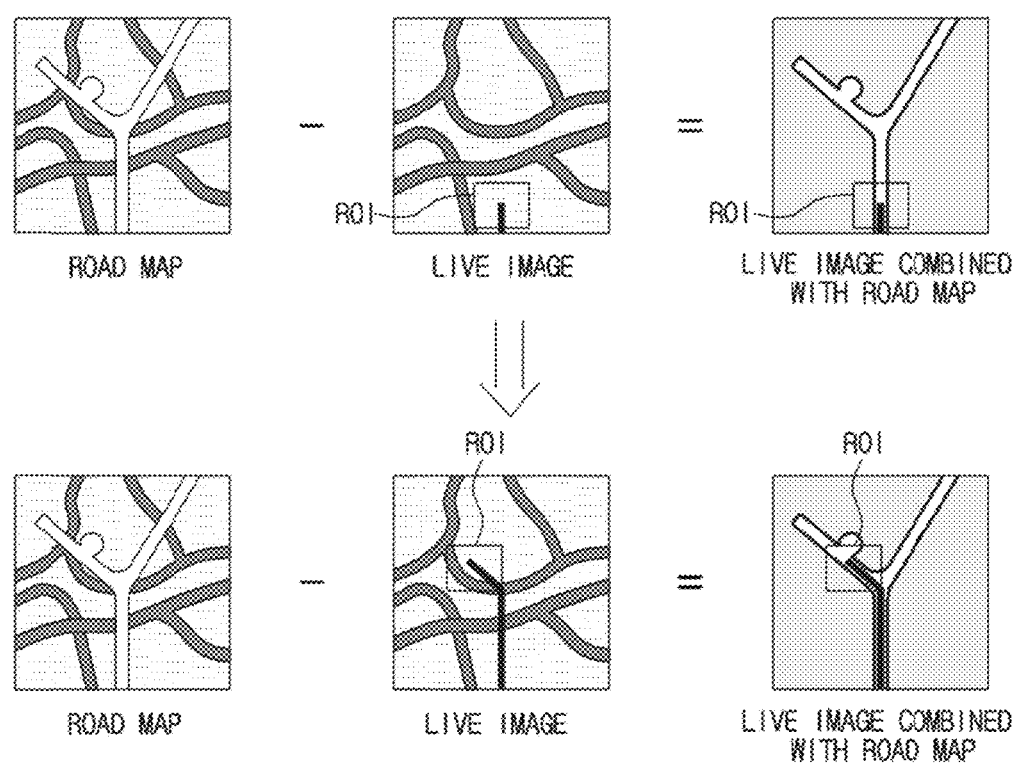
FIG. 12 is a diagram schematically illustrating a live image combined with a road map.

FIG. 12 is a diagram schematically illustrating a live image combined with a road map.

As illustrated in FIG. 12, first, a contrast agent is injected into a target blood vessel into which the instrument will be inserted and a road map mask is generated. The road map mask is a still image serving as a blood vessel map. The image processor 150 combines the road map mask with subsequent live fluoroscopic images, and may obtain an image in which the instrument overlaps the road map.

As an example, an image in which the subsequent live fluoroscopic image is subtracted from the road map mask to remove a background, and the instrument and the target blood vessel are represented in excellent contrast, may be obtained. Also, the road map mask may be subtracted from the subsequent live fluoroscopic image.

Before the road map mask and the live fluoroscopic image are combined, the image processor 150 may also perform digital subtraction angiography (DSA) on these images. In the DSA, an image before the contrast agent is injected is subtracted from an image after the contrast agent is injected, and a background anatomy or a tissue is removed, thereby increasing a recognition rate of the blood vessel.

Here, the live fluoroscopic image is an image in which X-rays having a low dose are incident on the non-ROI through real-time detecting and tracking of the ROI. When the live fluoroscopic image of a low dose is combined with the road map, the dose may decrease, and at the same time, a live image having excellent contrast between the blood vessel and the instrument may be obtained.

The image restorer 152 may perform image restoration or image enhancement for improving an image quality of the ROI of the image frame.

The image restorer 152 may restore the ROI of the image frame using denoising algorithms such as spatial filtering, temporal filtering, spatio-temporal filtering, and super-resolution reconstruction. Description of restoring the ROI will be described in detail below.

Also, the image restorer 152 may enhance the ROI of the image frame using detail enhancement algorithms such as an edge enhancement filter and a contrast enhancement algorithm based on a histogram or a wavelet.

Since X-rays of a low dose are incident on the non-ROI, the non-ROI of the image frame may have a low SNR. Therefore, the image restorer 152 performs a restoration operation for improving an image quality of the non-ROI. Hereinafter, an operation of restoring the non-ROI of the image frame will be described in detail with reference to FIGS. 13A and 13B.

Figure 13A:
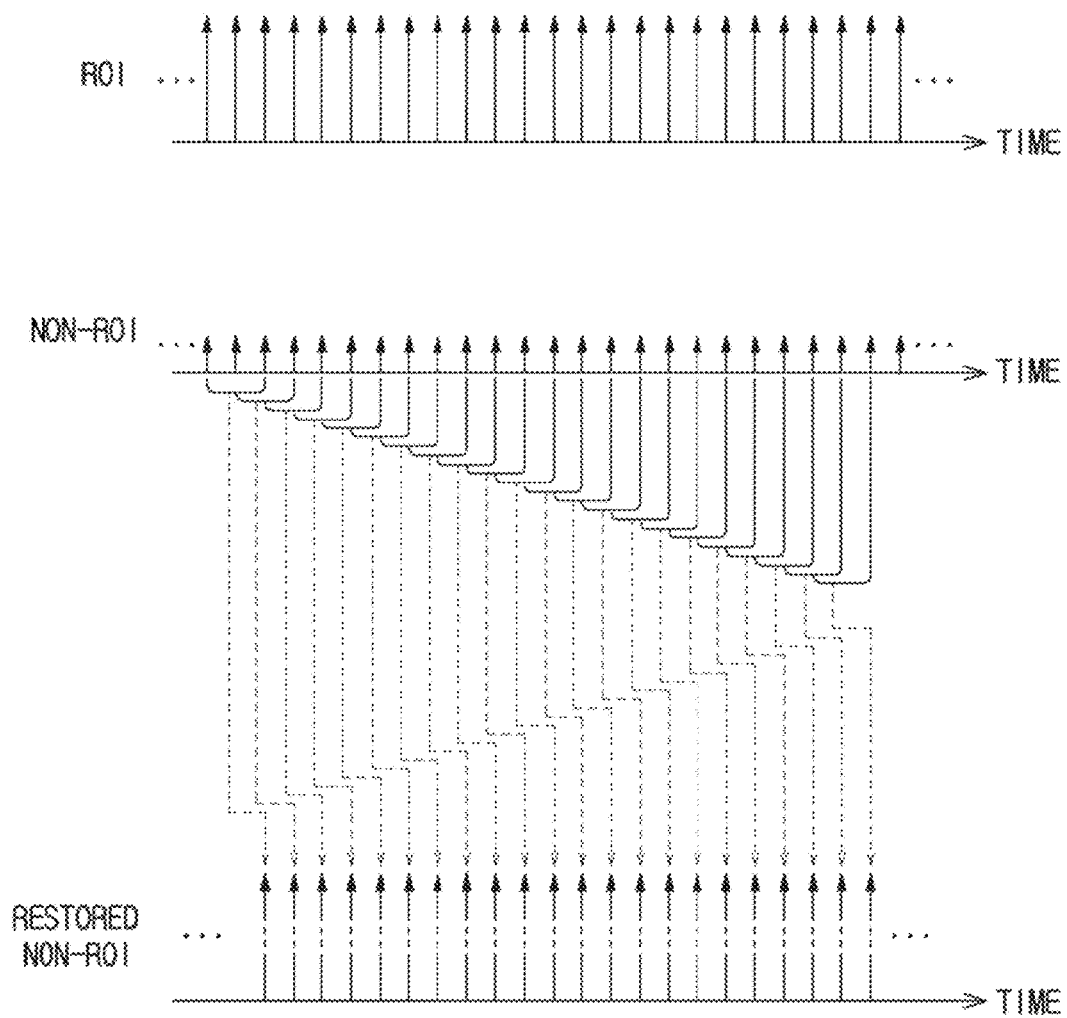
FIG. 13A is a diagram illustrating a process of restoring an image quality of an image frame by combining the image frame with a previous image.
Figure 13B:
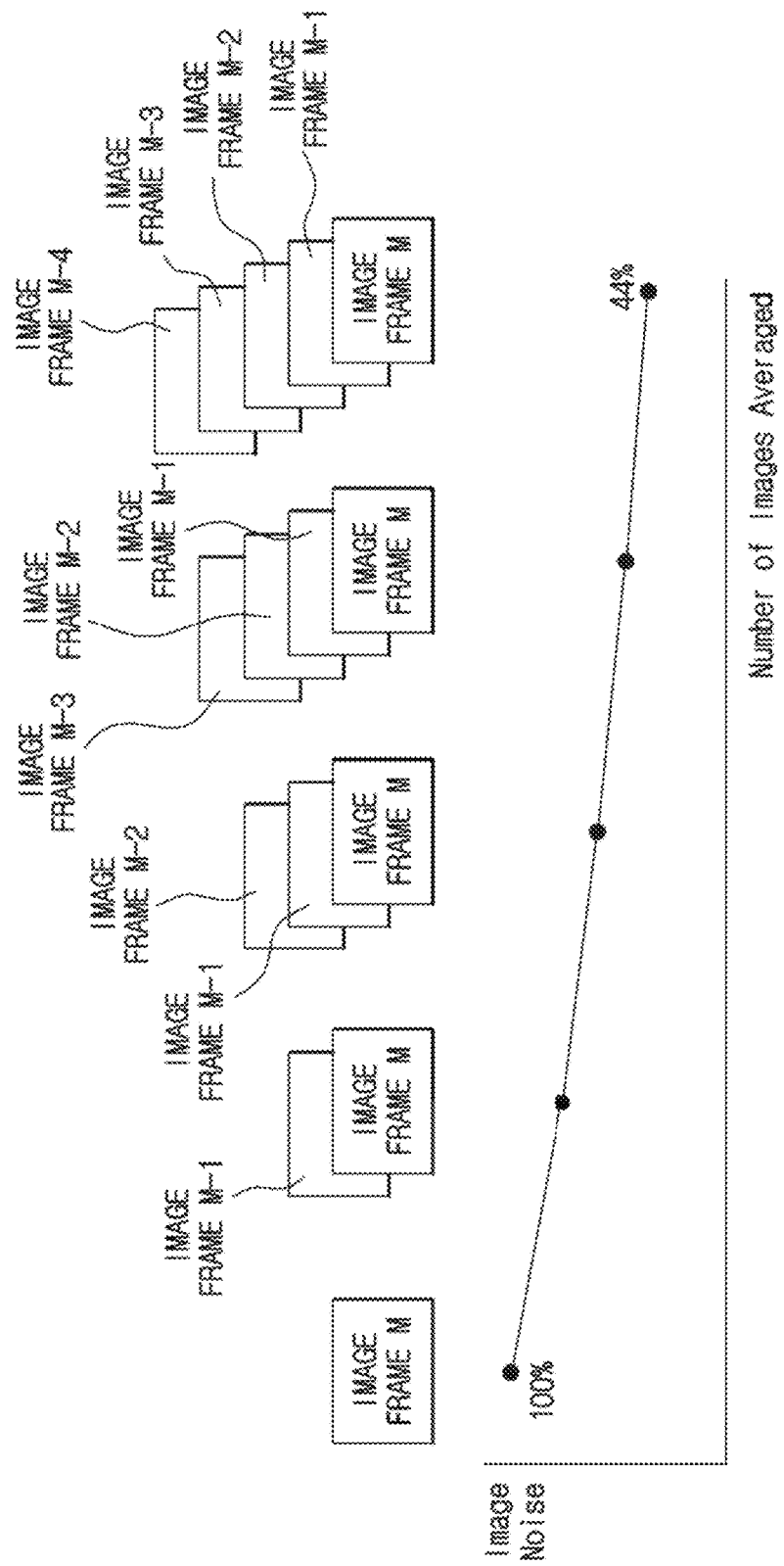
FIG. 13B is a diagram schematically illustrating an effect of decreasing noise of an image frame by averaging the image frame with a previous image.

FIG. 13A is a diagram illustrating a process of restoring an image quality of an image frame by combining the image frame with a previous image. FIG. 13B is a diagram schematically illustrating an effect of decreasing noise of an image frame by averaging the image frame with a previous image.

As illustrated in FIG. 13A, the image restorer 152 may perform image restoring to improve the image quality by combining a current image frame with at least one previous image frame. In this case, various combinations of image frames may be combined to perform image restoring on the non-ROI. As exemplified in FIG. 13A, a current image frame is combined with two previous image frames for restoration. Therefore, it is possible to obtain an image frame having an excellent SNR similar to an image frame of the ROI on which X-rays of a high dose are incident.

Exemplary methods of combining a current image frame with at least one previous image frame include a method of summing a current image frame and at least one previous image frame, a method of averaging a current image frame and at least one previous image frame, a method of applying motion-compensated temporal filtering or varying a filter to be applied to a current image frame in consideration of image characteristics such as an edge direction, and a method of applying motion-compensated spatial filtering. According to an exemplary embodiment, the summing may be simple summing or weighted summing, and the averaging may be simple averaging or weighted averaging.

The image restorer 152 may use one of the above methods or a combination thereof.

As illustrated in FIG. 13B, when the current image frame is an image frame m, the image frame m and an image frame m−1 may be averaged in order to restore the image frame m. As necessary, the image frame m and additional previous image frames may also be averaged.

As the number of previous images used for averaging increases, a noise decrease rate of the image increases. For example, when the image frame m and four previous image frames are averaged, noise may be decreased to about 60%. The image restorer 152 may determine the number of previous image frames used for averaging in consideration of noise, an image lag, and the like of the current image frame.

Also, the image restorer 152 may perform additional image enhancement on the non-ROI of the restored image frame. As an example, in order to reduce degradation of resolution and image blurring that can be generated when the current image frame and the previous image frame are combined, it is possible to perform alignment or registration between image frames or motion prediction and compensation.

As an algorithm for registering between image frames, a feature-based algorithm, an intensity-based algorithm, or an algorithm in which a feature and an intensity are mixed may be used.

As a motion field model for motion prediction and compensation, a translational motion, a block-based piecewise translational motion, rotation, scaling, a non-rigid deformable motion, and the like may be used.

Also, the image restorer 152 may perform image restoring on the ROI in addition to the non-ROI. In this case, image restoring may be performed on the ROI using a method of combining the current image frame with the previous image frame. When both the ROI and the non-ROI are restored, spatial filtering (spatial denoising filtering), temporal filtering (temporal denoising filtering), or both the spatial filtering and the temporal filtering may be performed on the both regions. Both the spatial filtering and the temporal filtering may be movement compensation filtering.

Also, according to each movement characteristic of the non-ROI and the ROI, appropriate filtering may be selected. As an example, when movement is large and fast, the spatial filtering may be applied, and otherwise, the temporal filtering may be applied. Therefore, when movement in the ROI is large or fast, the spatial filtering may be applied to the ROI, and the temporal filtering may be applied to the non-ROI.

Also, when the temporal filtering is applied to both the ROI and the non-ROI, a filtering strength may be differently applied, and therefore it may be possible to optimize an image quality of a full image including the ROI and the non-ROI. For example, when movement of the object of interest is large and a similarity between temporally adjacent image frames is low, an effect of filtering may decrease if the temporal filtering is applied. In this case, temporal filtering of a relatively low strength may be applied to the ROI, and temporal filtering of a relatively high strength may be applied to the non-ROI. Therefore, the image quality of the non-ROI to which X-rays of a relatively low dose are radiated is restored and it is possible to prevent the object of interest having complex movement from blurring.

In order to adjust the strength of the temporal filtering, the number of previous image frames used for restoring the current image frame may be adjusted or a weight applied to each previous image frame may be adjusted. For example, in order to apply temporal filtering of a low strength, a relatively small number of previous image frames may be used for restoring. Also, the same number of previous image frames as when filtering of a high strength is applied is used, but a weight applied to the previous image frame may be adjusted according to temporal proximity with the current image frame. For example, a higher weight may be applied to the previous image frame that is closest to the current image frame, and a lower weight may be applied to the previous image frame that is further from the current image frame.

Also, the image restorer 152 may perform an image equalization algorithm for matching brightness and contrast of the ROI and the non-ROI of the image frame.

When X-ray doses incident on the ROI and the non-ROI are changed according to X-ray filtering of the non-ROI, an artifact may be generated in a boundary region of two regions. Therefore, the image restorer 152 performs image processing in which a boundary correcting algorithm is applied to the boundary region of the ROI and the non-ROI. Therefore, it is possible to decrease the artifact generated in the boundary region.

Characteristics of the boundary region may be changed according to a material, a shape, a position, and the like of the ROI filter 141. Therefore, when the image restorer 152 applies the boundary correcting algorithm to the boundary region and performs image processing, the characteristic of the ROI filter 141 may be considered.

As an example of the boundary correcting algorithm applied by the image restorer 152, a linear blending algorithm may be used. The linear blending algorithm may also be called feathering or alpha blending. The linear blending algorithm is a method in which a weight is given to a value of each pixel in a region in which a boundary is generated and blending is performed. As a region in which the weight is given increases, a boundary region may be naturally formed.

As another example of the boundary correcting algorithm applied by the image restorer 152, a multi band blending algorithm may be used. The multi band blending algorithm is a method in which high frequency and low frequency images are separated for each band through a Gaussian pyramid, band images are separated based on a maximum weight function, a different weight is given to each band image, and blending is performed. Since a high frequency image is narrowly blended and a low frequency image is widely blended, it is possible to effectively blend detail components.

The above-described boundary correcting algorithms are only examples of the types of boundary correcting algorithms which may be applied according to exemplary embodiments. Types of the boundary correcting algorithms used by the image restorer 152 are not limited to these examples.

When the ROI filter 141 moves while X-rays are radiated, a pattern of the boundary region may be changed. Therefore, the image restorer 152 may use information on the movement speed or the position change of the ROI filter 141 when X-rays are radiated, estimate the pattern of the boundary region, and compensate for the boundary region using the estimated pattern.

Figure 14:
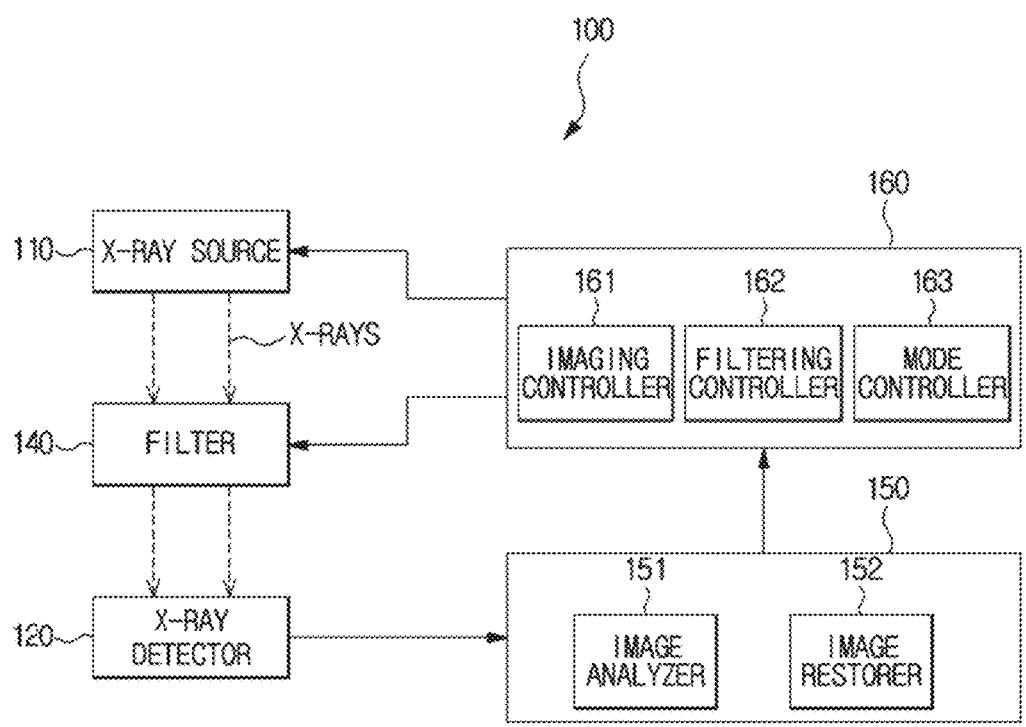
FIG. 14 is a control block diagram of an X-ray imaging apparatus that further includes a mode control unit.

FIG. 14 is a control block diagram of an X-ray imaging apparatus that further includes a mode control unit.

As illustrated in FIG. 14, the controller 160 of the X-ray imaging apparatus 100 may further include a mode controller 163 configured to control an X-ray imaging mode. The X-ray imaging mode that can be controlled by the mode controller 163 includes an ROI mode and a full imaging mode. As described above, the ROI mode is an imaging mode in which the ROI is detected and there is a difference between X-ray doses of the ROI and the non-ROI, and the full imaging (full FOV) mode is a general imaging mode in which there is no difference between X-ray doses of the ROI and the non-ROI and X-rays of a uniform dose are radiated onto the object region.

The mode controller 163 may control the X-ray imaging mode based on information on the image frame analyzed by the image analyzer 151, information on the imaging mode, or information on a stage. When the X-ray imaging mode is controlled, the mode controller 163 may consider all or some pieces of information.

The information on the image frame may include information on the ROI or information on the image characteristics. Hereinafter, an operation of the mode controller 163 controlling the X-ray imaging mode based on the information on the ROI will be described in detail.

The information on the ROI includes the movement characteristics of the object of interest, and the mode controller 163 may control the X-ray imaging mode based on the movement size of the object of interest.

Specifically, when the movement of the object of interest is large, radiating X-rays of a uniform dose onto the full imaging region may be more efficient than manually changing an X-ray radiation amount for each region according to the movement of the object of interest. Therefore, when the movement of the object of interest is large, the mode controller 163 sets the X-ray imaging mode as the full imaging mode, and enables X-rays of a uniform dose to be radiated onto the full imaging region.

The mode controller 163 may compare the movement size of the object of interest and a predetermined reference value to determine whether the movement size is large. The reference value may be set based on an experiment, statistics, a simulation, a theory, and the like. In order to distinguish a reference value from other reference values, the reference value that can be used to determine whether the movement size is large and that serves as a setting reference of the full imaging mode is referred to as a first reference value.

When the movement of the object of interest is not large, the mode controller 163 may set the X-ray imaging mode as the ROI mode. The ROI mode may be further divided into two modes based on the movement size of the object of interest.

When the movement of the object of interest is small, the X-ray radiation amount for each region should be finely changed. Only a size of the ROI may be increased by a certain degree to include the movement of the object of interest, which may be more efficient. In this exemplary embodiment, the X-ray imaging mode in which such operations are performed is referred to as a stationary mode. When the movement size of the object of interest is less than a predetermined second reference value, the mode controller 163 may set the X-ray imaging mode as the stationary mode.

Also, when the movement of the object of interest is in an intermediate level, in other words, when the movement size of the object of interest is greater than the predetermined second reference value, the mode controller 163 sets the X-ray imaging mode as an imaging mode in which the ROI is moved according to the movement of the object of interest, the ROI filter 141 is moved to a position corresponding to the non-ROI, and an X-ray radiation amount is adjusted. This imaging mode is referred to as a dynamic mode.

The mode controller 163 may set the X-ray imaging mode as any two modes or any one mode of the above-described full imaging mode, stationary mode, and dynamic mode.

Specifically, the mode controller 163 may set the X-ray imaging mode as the full imaging mode when the movement size of the object of interest is greater than a predetermined third reference value, and may set the X-ray imaging mode as the stationary mode when the movement size of the object of interest is less than the predetermined third reference value. The predetermined third reference value may be the same value as or a different value from the first reference value or the second reference value.

Also, when the movement size of the object of interest is greater than a predetermined fourth reference value, the X-ray imaging mode may be set as the full imaging mode, and when the movement size of the object of interest is less than the predetermined fourth reference value, the X-ray imaging mode may be set as the dynamic mode. The fourth reference value may be the same value as or a different value from the first reference value, the second reference value, or the third reference value.

Also, when the movement size of the object of interest is greater than a predetermined fifth reference value, the X-ray imaging mode may be set as the dynamic mode, and when the movement size of the object of interest is less than the predetermined fifth reference value, the X-ray imaging mode may be set as the stationary mode. The fifth reference value may be the same value as or a different value from the first reference value, the second reference value, the third reference value, or the fourth reference value.

Also, regardless of the movement size of the object of interest, the X-ray imaging mode may be set as only the stationary mode or only the dynamic mode.

Hereinafter, an operation of the mode controller 163 controlling the X-ray imaging mode based on information on the imaging mode or information on the stage will be described.

The imaging mode that can be performed by the X-ray imaging apparatus 100 includes a general X-ray fluoroscopic mode, a DSA mode, and the like.

A DSA image obtained by the DSA mode may be beneficially used to recognize a position or a shape of the observation target blood vessel in a full object region. When the imaging mode of the X-ray imaging apparatus 100 is the DSA mode, the mode controller 163 may set the X-ray imaging mode as the full imaging mode.

Also, in the X-ray fluoroscopic mode, the ROI mode may be set. Therefore, the dynamic mode or the stationary mode may be set according to the movement characteristic of the object of interest. As described above, however, when the movement of the object of interest is large, the full imaging mode may also be set.

The information on the stage includes information indicating a current operation among several operations for X-ray imaging. For example, information indicating a catheter inserting operation, a stent inserting operation, or a contrast agent injecting operation may be the information on the stage.

As an example, if the imaging mode is the X-ray fluoroscopic mode, when the current operation is the contrast agent injecting operation, the X-ray imaging mode may be set as the full imaging mode in order to recognize an entire structure of the subject.

The information on the imaging mode or the information on the stage may be determined by a device or may be input by the user. The mode controller 163 may set the X-ray imaging mode according to whether full image information is important or image information of the ROI is important based on various pieces of information input by the user in addition to the above-described example.

Figure 15:
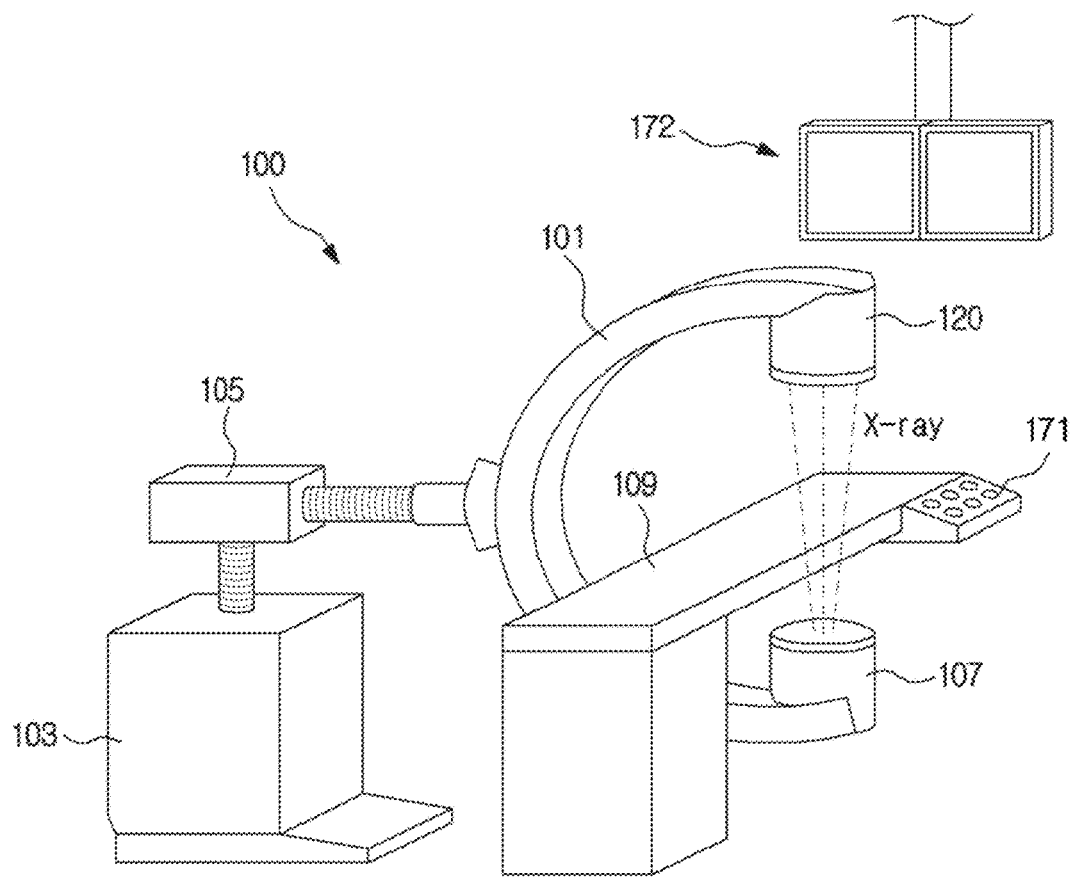
FIG. 15 is a diagram illustrating an appearance of an X-ray imaging apparatus according to an exemplary embodiment.

FIG. 15 is a diagram illustrating an appearance of an X-ray imaging apparatus according to an exemplary embodiment.

As an example, the X-ray imaging apparatus 100 may have a C-arm structure as illustrated in FIG. 15. An X-ray source assembly 107 and the X-ray detector 120 may be provided in each end of a C-arm 101 having a C shape. The C-arm 101 is connected to a main body 103 through a connecting shaft 105 and is rotatable in an orbital direction.

An inside of the X-ray source assembly 107 may include the X-ray source 110, the collimator 131, and the filter 140. A patient table 109 is provided between the X-ray source assembly 107 and the X-ray detector 120. When the object is positioned on the patient table 109, the X-ray source 110 radiates X-rays onto the subject, the X-ray detector 120 detects the radiated X-rays, and thereby the X-ray image of the object is obtained.

As described above, the X-ray imaging apparatus 100 may perform X-ray imaging according to various imaging modes and obtain a live video of the subject. The user may perform operations or determine a diagnosis while watching a display unit 172 that has a plurality of screens and can display several images to be used for operations or diagnosis.

As described above, when the image analyzer 151 obtains the information on the ROI, the imaging controller 161 sets the imaging parameter, or the mode controller 163 controls the X-ray imaging mode, information input by the user may be used. The user may input information through an input unit 171 (e.g., inputter) provided in the X-ray imaging apparatus 100.

Hereinafter, an exemplary embodiment of a method of controlling an X-ray imaging apparatus will be described.

Figure 16:
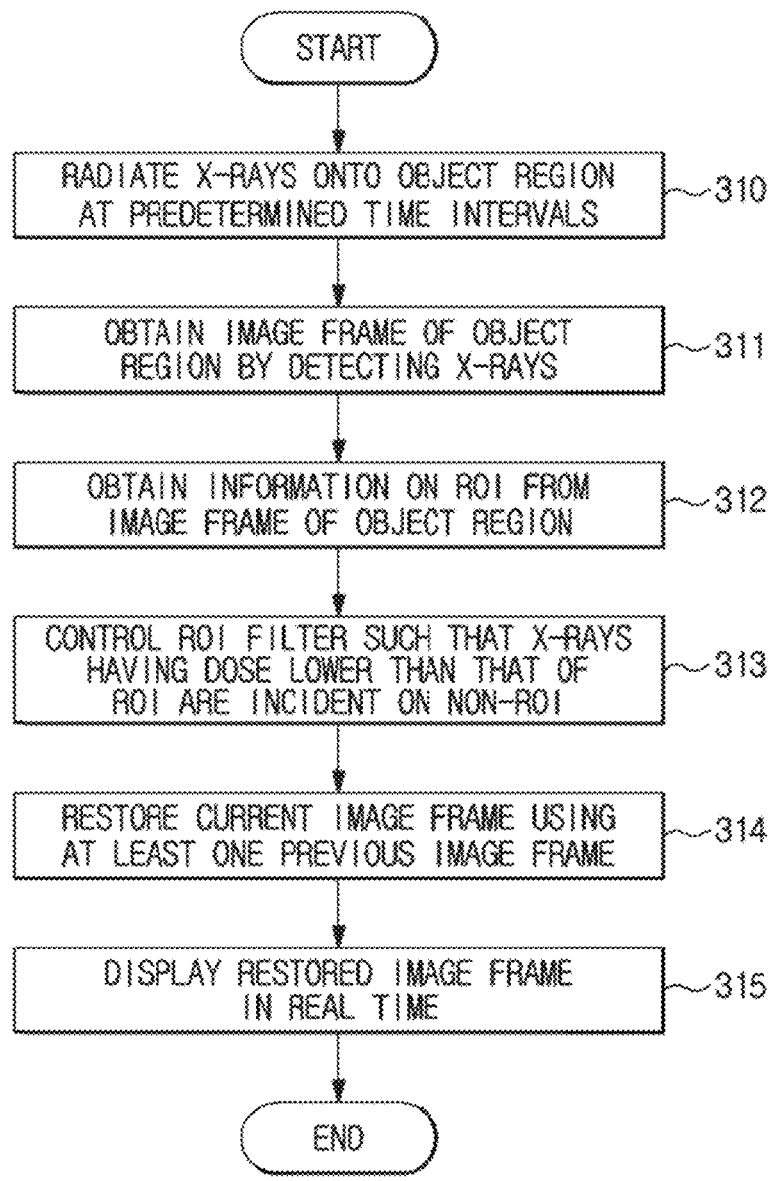
FIG. 16 is a flowchart illustrating a method of controlling an X-ray imaging apparatus according to an exemplary embodiment.

FIG. 16 is a flowchart illustrating a method of controlling an X-ray imaging apparatus according to an exemplary embodiment. The above-described X-ray imaging apparatus 100 may be used to perform the control method according to the exemplary embodiment.

As illustrated in FIG. 16, X-rays are radiated onto the object region at predetermined time intervals at operation 310. X-rays can be continuously radiated. However, in this exemplary embodiment, in order to reduce the X-ray dose and improve temporal resolution, the pulse exposure method in which X-rays are radiated at predetermined time intervals is used. The predetermined time interval may be determined by a pulse rate. For example, when the pulse rate is 30 pulses per second (30 pps), X-rays are radiated 30 times per second.

The image frame of the object region is obtained by detecting the radiated X-rays at operation 311. The object region may match an X-ray imaging region, and obtaining of the image frame may be synchronized with radiation of X-rays and performed in real time.

Information on the ROI is obtained from the image frame of the object region at operation 312. The obtaining of the information on the ROI includes detection of the object of interest and setting of the ROI based on the detected object of interest. Specifically, the object of interest is detected from the image frame of the object region, and a predetermined region including the detected object of interest is set as the ROI. A position and a size of the ROI may be determined in consideration of a position and a size of the object of interest or the movement characteristic of the object of interest. Uncertainty included in the movement characteristic of the object of interest may also be considered. The information on the ROI includes the position, the size, or the movement characteristic of the ROI, and the movement characteristic of the ROI may be defined by the movement characteristic of the object of interest.

The ROI filter is controlled such that X-rays having a dose lower than a dose of X-rays incident on the ROI are incident on the non-ROI at operation 313. The ROI filter 141 is disposed between the X-ray source 110 configured to radiate X-rays and the X-ray detector 120 configured to detect X-rays such that position control is possible. Therefore, the ROI filter 141 is positioned at a position corresponding to the non-ROI such that X-rays having a dose lower than a dose of X-rays incident on the ROI may be incident on the non-ROI. Setting of the ROI may be performed in real time according to the frame rate. When the ROI moves, this movement is tracked, and the ROI filter 141 is moved to the position corresponding to the non-ROI.

A control operation of the ROI filter may include adjustment of a difference between X-ray doses to be incident on the ROI and the non-ROI based on image characteristics of the ROI and the non-ROI such as noise, motion, and contrast.

Since X-rays of a low dose are incident on the non-ROI, the non-ROI of the image frame has a low SNR. Therefore, a current image frame is restored using at least one previous image frame to improve an image quality of the non-ROI at operation 314. Specifically, the current image frame may be combined with at least one previous image frame. Exemplary methods of combining a current image frame with a previous image frame include a method of averaging or summing a current image frame and a previous image frame, a method of variably applying a filter to be applied to the current image frame in consideration of image characteristics represented in the previous image frame such as noise and an edge direction, a method of applying motion-compensated temporal filtering, and a method of applying motion-compensated spatial filtering. Various combinations of images may be combined to perform the restoring on the non-ROI.

Also, additional image enforcement may be performed on the restored image frame. For example, in order to reduce degradation of resolution and image blurring that can be generated when the current image frame and the previous image frame are combined, alignment or registration between image frames, or motion prediction and compensation, may be performed.

Restoration work for improving an image quality of the image may also be performed on the ROI of the image frame, and the ROI of the image frame may be restored using denoising algorithms such as a spatial filter, a temporal filter, a spatio-temporal filter, and super-resolution reconstruction. The ROI of the image frame may be enhanced using a detail enhancement algorithm such as an edge enhancement filter and a contrast enhancement algorithm based on a histogram or a wavelet.

Also, an image equalization algorithm for matching brightness and contrast of the ROI and the non-ROI of the image frame is performed, and the restored image frame is displayed in the display unit in real time at operation 315.

The method of controlling an X-ray imaging apparatus according to an exemplary embodiment may automatically control the X-ray imaging mode based on information on the image frame, information on the imaging mode, or information on the stage. Hereinafter, an exemplary embodiment in which the X-ray imaging mode is controlled based on the movement size of the object of interest, among the various types of information of the image frame, will be described.

Figure 17:
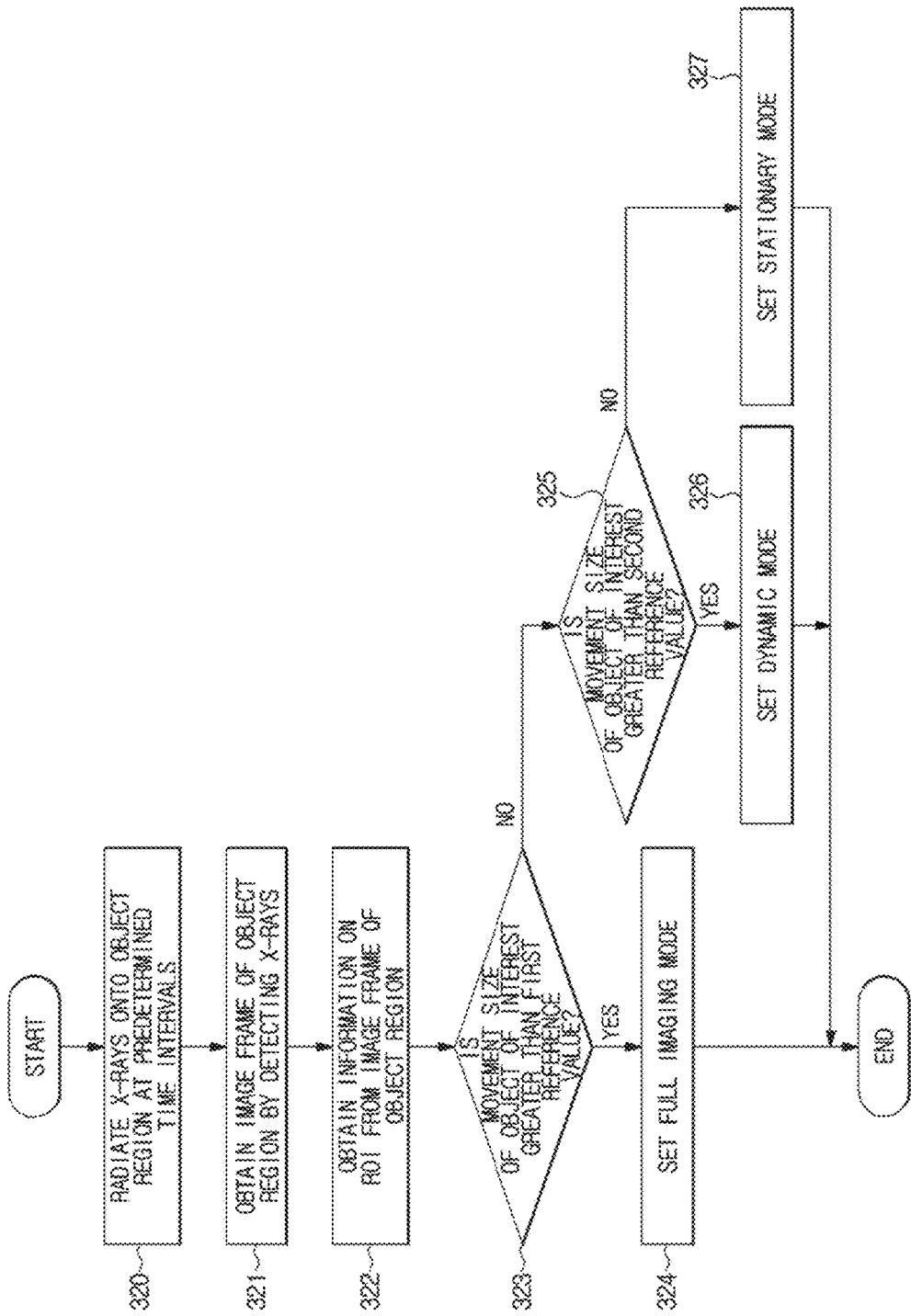
FIG. 17 is a flowchart illustrating an example of controlling an X-ray imaging mode when performing the method of controlling an X-ray imaging apparatus.

FIG. 17 is a flowchart illustrating an example of controlling an X-ray imaging mode when performing the method of controlling an X-ray imaging apparatus.

As illustrated in FIG. 17, X-rays are radiated onto the object region at predetermined time intervals at operation 320, and the image frame of the object region is obtained by detecting the radiated X-rays at operation 321. Information on the ROI is obtained from the image frame of the object region at operation 322. According to an exemplary embodiment, the information on the ROI includes information indicating the movement size of the object of interest.

When the movement size of the object of interest is greater than a first reference value (Yes in operation 323), the X-ray imaging mode is set as the full imaging mode in operation 324, and resulting X-ray imaging is performed.

The full imaging (full FOV) mode is a general imaging mode in which there is no difference between X-ray doses of the ROI and the non-ROI.

When the movement size of the object of interest is less than the first reference value (No in operation 323), the system determines whether the movement size of the object of interest is greater than a second reference value at operation 325. When the movement size of the object of interest is greater than the second reference value (Yes in operation 325), the X-ray imaging mode is set as the dynamic mode at operation 326, and resulting X-ray imaging is performed. The dynamic mode is a mode in which the ROI is moved according to the movement of the object of interest, among the ROI modes in which there is a difference between X-ray doses of the ROI and the non-ROI.

When the movement size of the object of interest is less than the second reference value (No in operation 325), the X-ray imaging mode is set as the stationary mode in operation 327, and resulting X-ray imaging is performed. The stationary mode is a mode in which only a size of the ROI is increased by a certain degree to include the movement of the object of interest with no movement.

Figure 18:
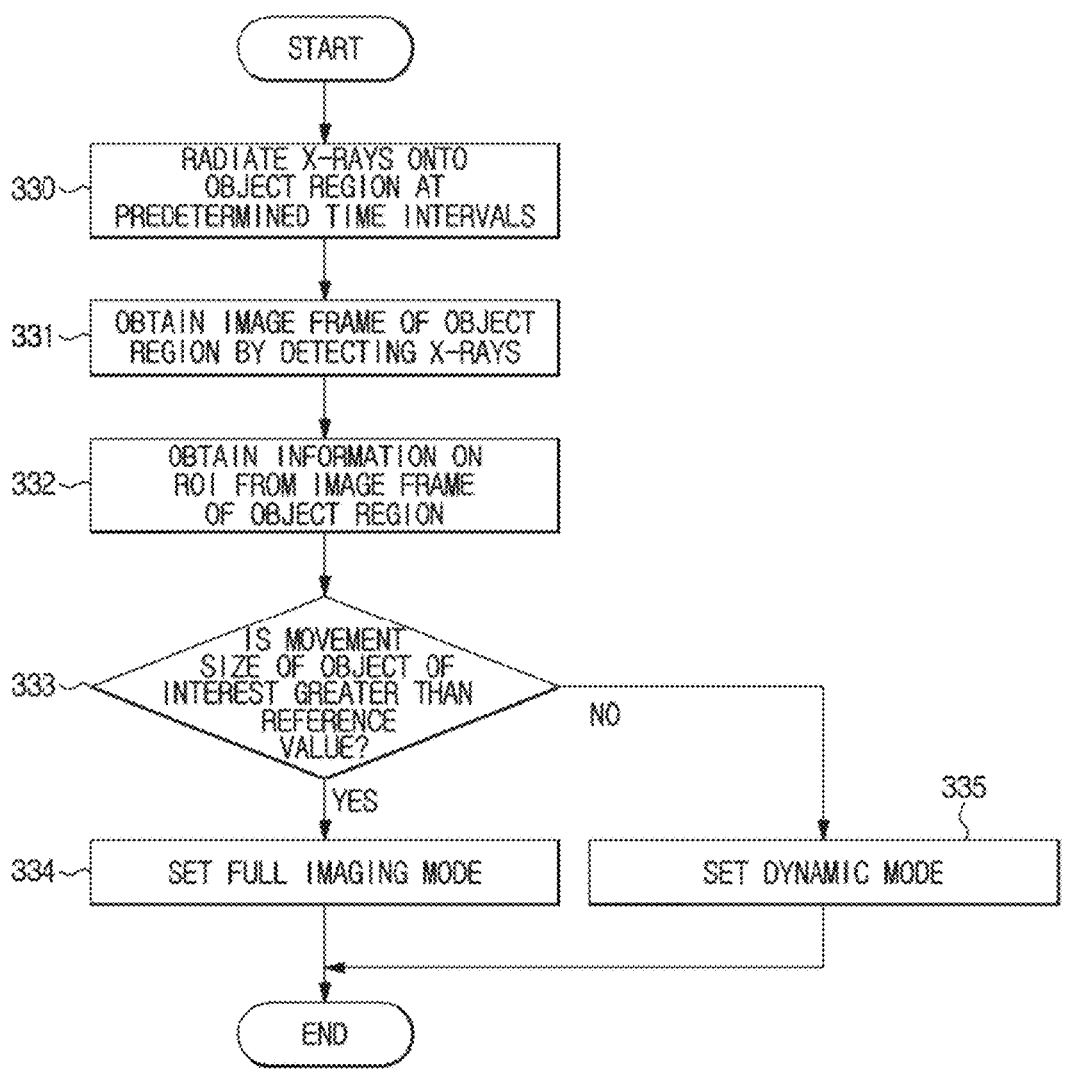
FIG. 18 is a flowchart illustrating another example of controlling an X-ray imaging mode when performing the method of controlling an X-ray imaging apparatus.

FIG. 18 is a flowchart illustrating another example of controlling an X-ray imaging mode when performing the method of controlling an X-ray imaging apparatus.

As illustrated in FIG. 18, X-rays are radiated onto the object region at predetermined time intervals at operation 330), and the image frame of the object region is obtained by detecting the radiated X-rays at operation 331). Information on the ROI is obtained from the image frame of the object region at operation 332). According to an exemplary embodiment, the information on the ROI includes the movement size of the object of interest.

When the movement size of the object of interest is greater than a reference value (Yes in operation 333), the X-ray imaging mode is set as the full imaging mode at operation 334, and resulting X-ray imaging is performed.

When the movement size of the object of interest is less than the reference value (No in operation 333), the X-ray imaging mode is set as the dynamic mode at operation 335, and resulting X-ray imaging is performed. According to an exemplary embodiment, the reference value may be the same value as or a different value from the first reference value or the second reference value in the example of FIG. 17.

Figure 19:
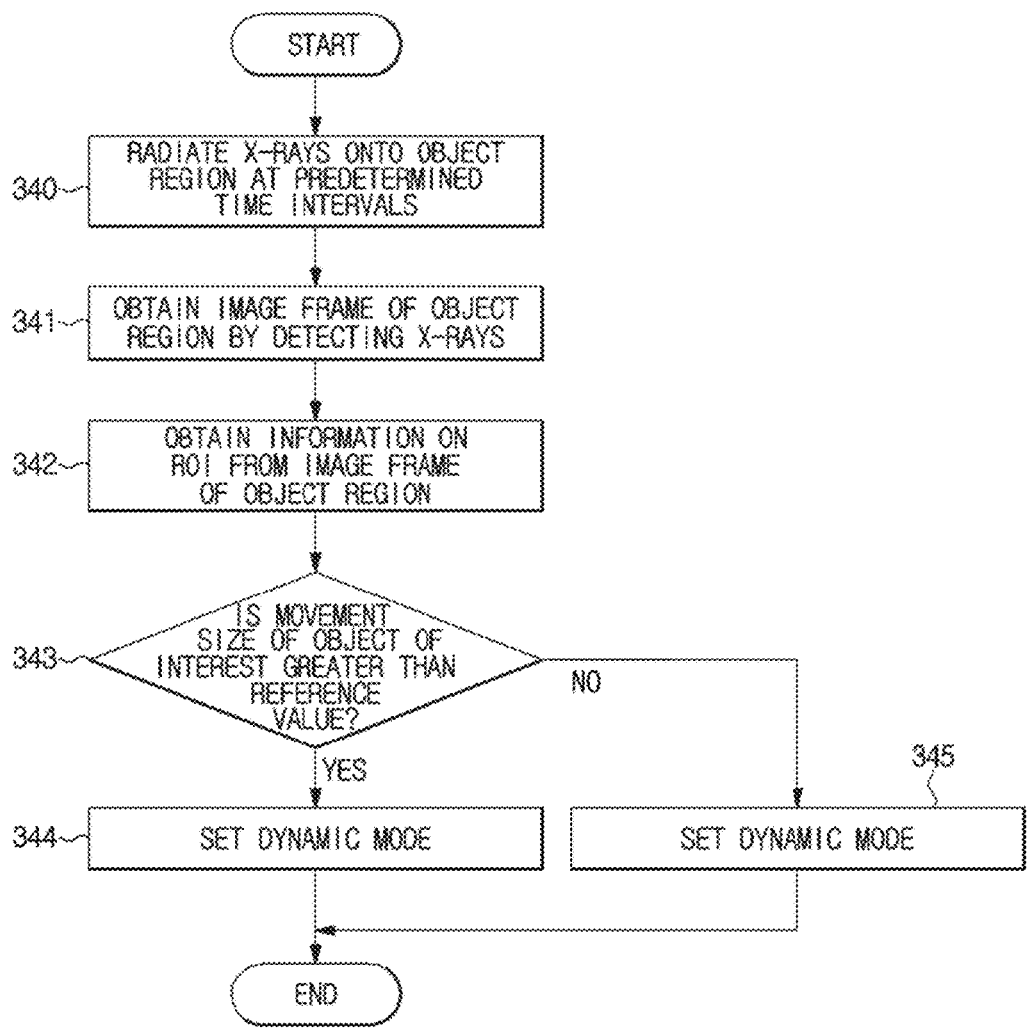
FIG. 19 is a flowchart illustrating still another example of controlling an X-ray imaging mode when performing the method of controlling an X-ray imaging apparatus.

FIG. 19 is a flowchart illustrating still another example of controlling an X-ray imaging mode when performing the method of controlling an X-ray imaging apparatus.

As illustrated in FIG. 19, X-rays are radiated onto the object region at predetermined time intervals at operation 340, and the image frame of the object region is obtained by detecting the radiated X-rays at operation 341. Information on the ROI is obtained from the image frame of the object region at operation 342. According to an exemplary embodiment, the information on the ROI includes the movement size of the object of interest.

When the movement size of the object of interest is greater than a reference value (Yes in operation 343), the X-ray imaging mode is set as the dynamic mode at operation 344, and resulting X-ray imaging is performed.

When the movement size of the object of interest is less than the reference value (No in operation 343), the X-ray imaging mode is set as the stationary mode at operation 345, and resulting X-ray imaging is performed. According to an exemplary embodiment, the reference value may be the same value as or a different value from the first reference value or the second reference value in the example of FIG. 17 or the reference value in the example of FIG. 18.

Figure 20:
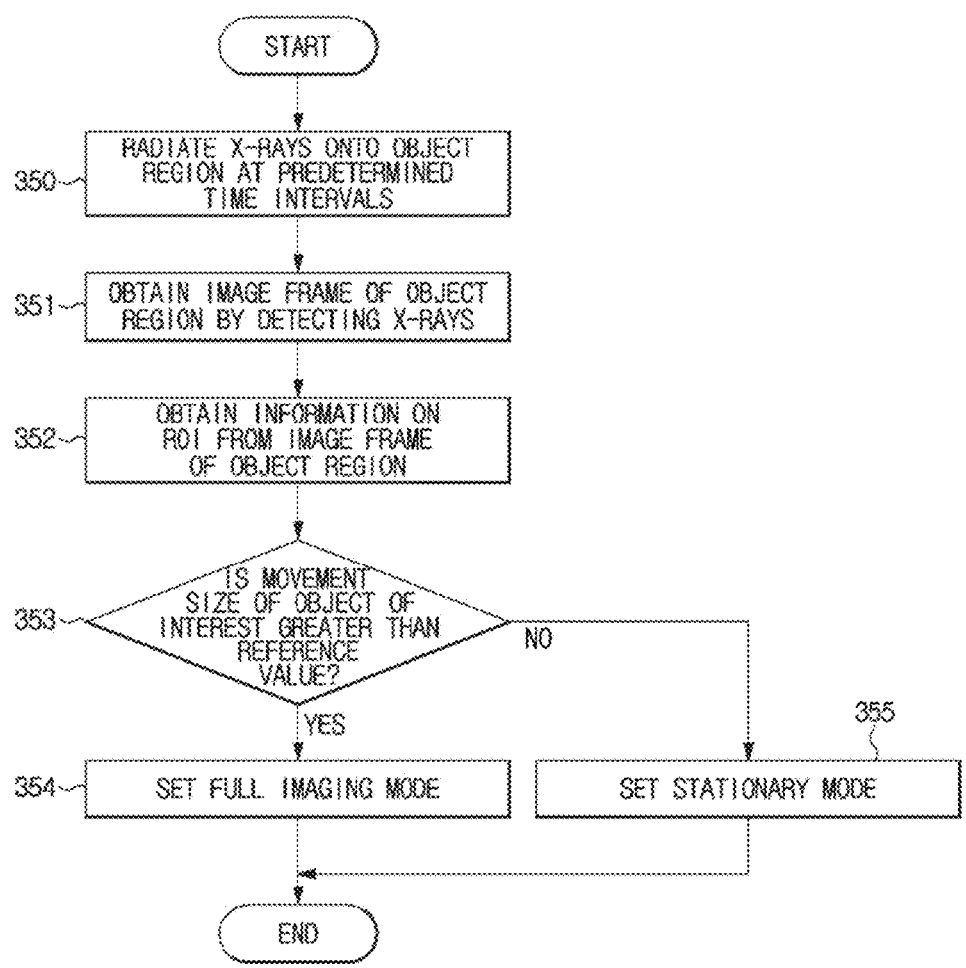
FIG. 20 is a flowchart illustrating yet another example of controlling an X-ray imaging mode when performing the method of controlling an X-ray imaging apparatus.

FIG. 20 is a flowchart illustrating yet another example of controlling an X-ray imaging mode when performing the method of controlling an X-ray imaging apparatus.

As illustrated in FIG. 20, X-rays are radiated onto the object region at predetermined time intervals at operation 350, and the image frame of the object region is obtained by detecting the radiated X-rays at operation 351. Information on the ROI is obtained from the image frame of the object region at operation 352. According to an exemplary embodiment, the information on the ROI includes the movement size of the object of interest.

When the movement size of the object of interest is greater than a reference value (Yes in operation 353), the X-ray imaging mode is set as the full imaging mode at operation 354), and resulting X-ray imaging is performed.

When the movement size of the object of interest is less than the reference value (No in operation 353), the X-ray imaging mode is set as the stationary mode at operation 355, and resulting X-ray imaging is performed. According to an exemplary embodiment, the reference value may be the same value as or a different value from the first reference value or the second reference value in the example of FIG. 17, the reference value in the example of FIG. 18, or the reference value in the example of FIG. 19.

Also, according to another example of controlling the X-ray imaging mode, regardless of the movement size of the object of interest, the X-ray imaging mode may be set as only the stationary mode or only the dynamic mode.

Hereinafter, an exemplary method of controlling an X-ray imaging apparatus in which the X-ray imaging mode is controlled based on information on the imaging mode or information on the stage will be described.

The imaging mode includes a general X-ray fluoroscopic mode, a DSA mode, and the like. The information on the stage may include information indicating whether a current operation is a catheter inserting operation, a stent inserting operation, or a contrast agent injecting operation among several operations for X-ray imaging.

As an example, when the imaging mode is the DSA mode, the X-ray imaging mode is set as the full imaging mode. When the imaging mode is the X-ray fluoroscopic mode, the X-ray imaging mode may be set as the ROI mode that is set as a default between the dynamic mode and the stationary mode.

In the X-ray fluoroscopic mode, as illustrated in FIGS. 17 to 20, any mode among the full imaging mode, the dynamic mode, and the stationary mode may also be set based on the movement size of the object of interest.

According to the X-ray imaging apparatus and the method of controlling the same described above, X-rays of a low dose are incident on the non-ROI to decrease a total X-ray dose, and image restoration is performed on the non-ROI of the image frame to improve an image quality that is degraded due to X-rays of a low dose. Therefore, it is possible to decrease the X-ray dose and obtain the X-ray image of high quality.

Also, the ROI filter is automatically moved according to the position of the ROI, and separate user manipulation is not required, thereby ensuring continuity of operation procedures using the X-ray imaging apparatus.

It is possible to obtain an X-ray video in which an X-ray dose decreases but an image quality decrease of an X-ray image and an FOV loss are minimized.

While the exemplary embodiments have been shown and described with reference to certain exemplary embodiments thereof, it will be understood by those skilled in the art that various modifications in form and details may be made therein without departing from the spirit and scope of the exemplary embodiments as defined by the appended claims.

What is claimed is:

1. An X-ray imaging apparatus comprising:
   an X-ray source configured to radiate X-rays onto an object region including an object of interest;
   an X-ray detector configured to detect the radiated X-rays and obtain image frames of the object region based on the detected X-rays;
   a filter configured to filter the X-rays radiated from the X-ray source such that the X-rays incident on a non-region of interest (ROI) of the object region have a lower dose than a dose of the X-rays incident on an ROI of the object region; and
   a controller configured to set an X-ray imaging mode according to a movement characteristic of the object of interest.

2. The X-ray imaging apparatus according to claim 1, further comprising:
   an image processor configured to set the ROI using the image frames, combine a current image frame, of the image frames, obtained when X-rays of the lower dose are incident on the non-ROI with a previous image frame of the image frames, and perform image restoring on the non-ROI of the current image frame based on the combined image frames.

3. The X-ray imaging apparatus according to claim 2, wherein the controller is further configured to control the filter, and
   wherein the image processor is configured to obtain information about the ROI from the current image frame and transmit the information to the controller.

4. The X-ray imaging apparatus according to claim 2, wherein the filter includes:
   an ROI filter made of a filtration material that reduces the X-rays; and
   a filter driver configured to move the ROI filter.

5. The X-ray imaging apparatus according to claim 2, wherein the image processor is configured to detect an object of interest from the current image frame, and set the ROI based on a position, a size, or a movement characteristic of the object of interest.

6. The X-ray imaging apparatus according to claim 5, wherein the image processor is configured to detect the object of interest by detecting a marker attached to the object of interest, from the image frame.

7. The X-ray imaging apparatus according to claim 5, wherein the image processor is configured to estimate a periodic movement pattern of the object region and reset the ROI using the estimated movement pattern.

8. The X-ray imaging apparatus according to claim 4, further comprising:
   an object of interest detector configured to detect an object of interest.

9. The X-ray imaging apparatus according to claim 8, wherein the controller is configured to turn on the filter driver based on a position of the object of interest.

10. The X-ray imaging apparatus according to claim 4, wherein the image processor is configured to estimate a movement direction and a movement speed of an object of interest based on a position of the object of interest, and
    the controller is configured to move the ROI filter in advance according to the estimated movement direction and movement speed of the object of interest.

11. The X-ray imaging apparatus according to claim 5, wherein the image processor is configured to detect the object of interest and set the ROI in real time according to a frame rate of the X-ray imaging apparatus.

12. The X-ray imaging apparatus according to claim 3, wherein the image processor is configured to detect the object of interest from the image frame, set the ROI based on a position, a size, or the movement characteristic of the object of interest, obtain information about the set ROI, and transmit the information about the set ROI to the controller, and
    the information about the set ROI may be at least one of a position of the ROI, a size of the ROI, and the movement characteristic of the ROI.

13. The X-ray imaging apparatus according to claim 12, wherein the filter includes:
    an ROI filter made of a filtration material that reduces X-rays; and
    a filter driver configured to move the ROI filter, and
    wherein the controller is configured to control the filter driver to move the ROI filter to a position corresponding to a position of the non-ROI based on the information about the set ROI.

14. The X-ray imaging apparatus according to claim 2, wherein the image processor is configured to perform the image restoring by at least one of averaging the current image frame and the previous image frame, summing the current image frame and the previous image frame, and applying motion-compensated temporal filtering or motion-compensated spatial filtering to the current image frame and the previous image frame.

15. The X-ray imaging apparatus according to claim 14 wherein the image processor is configured to perform the image restoring on the non-ROI and the ROI.

16. The X-ray imaging apparatus according to claim 15, wherein the image processor is configured to select a type of filtering applied to the non-ROI and the ROI based on a movement characteristic of an object of interest.

17. The X-ray imaging apparatus according to claim 2, wherein the image processor is configured to perform image registration or motion estimation and compensation on the non-ROI on which the image restoring is performed by combining the current image frame with the previous image frame.

18. The X-ray imaging apparatus according to claim 2, wherein the image processor is configured to use an image equalization algorithm for matching brightness and contrast of the ROI and the non-ROI of the current image frame on which the image restoring is performed on the non-ROI.

19. The X-ray imaging apparatus according to claim 13, wherein the controller is configured to set the X-ray imaging mode based on information about the current image frame, information about an imaging mode, or information about a stage of an X-ray imaging operation.

20. The X-ray imaging apparatus according to claim 19, wherein the information about the current image frame includes the information about the set ROI.

21. The X-ray imaging apparatus according to claim 20, wherein the controller is configured to set the X-ray imaging mode as one of a full imaging mode in which the X-rays of a uniform dose are radiated onto the ROI and the non-ROI and an ROI mode in which the X-rays having the lower dose than the dose of the ROI are radiated onto the non-ROI according to the movement characteristic of the object of interest.

22. The X-ray imaging apparatus according to claim 21, wherein, in response to the movement characteristic of the object of interest being greater than a first reference value, the controller is configured to set the X-ray imaging mode to the full imaging mode.

23. The X-ray imaging apparatus according to claim 22, wherein, in response to the movement characteristic of the object of interest being equal to or less than the first reference value, the controller is configured to set the X-ray imaging mode to the ROI mode.

24. The X-ray imaging apparatus according to claim 23, wherein, in response to the movement characteristic of the object of interest being equal to or less than the first reference value and greater than a second reference value, the controller is configured to set the X-ray imaging mode to a dynamic mode in which the ROI is moved according to a movement of the object of interest.

25. The X-ray imaging apparatus according to claim 24, wherein, in response to the movement characteristic of the object of interest being equal to or less than the second reference value, the controller is configured to set the X-ray imaging mode to a stationary mode in which a size of the ROI is increased according to the movement of the object of interest and a position of the ROI remains fixed.

26. The X-ray imaging apparatus according to claim 20, wherein, according to the movement characteristic of the object of interest, the controller is configured to set the X-ray imaging mode as one of a full imaging mode in which the X-rays of a uniform dose are radiated onto the object region and a dynamic mode in which the ROI is moved according to a movement of the object of interest.

27. The X-ray imaging apparatus according to claim 26, wherein the controller is configured to set the X-ray imaging mode to the dynamic mode in response to the movement characteristic of the object of interest being equal to or less than a reference value, and set the X-ray imaging mode to the full imaging mode in response to the movement characteristic of the object of interest being greater than the reference value.

28. The X-ray imaging apparatus according to claim 20, wherein the controller is configured to set the X-ray imaging mode as one of a full imaging mode in which the X-rays of a uniform dose are radiated onto the object region and a stationary mode in which a size of the ROI is increased according to a movement of the object of interest and a position of the ROI remains fixed according to the movement characteristic of the object of interest.

29. The X-ray imaging apparatus according to claim 28, wherein the controller is configured to set the X-ray imaging mode to the stationary mode in response to the movement characteristic of the object of interest being equal to or less than a reference value, and set the X-ray imaging mode to the full imaging mode in response to the movement characteristic of the object of interest being greater than the reference value.

30. The X-ray imaging apparatus according to claim 20, wherein, according to the movement characteristic of the object of interest, the controller is configured to set the X-ray imaging mode to one of a dynamic mode in which the ROI is moved according to a movement of the object of interest and a stationary mode in which a size of the ROI is increased according to the movement of the object of interest and a position of the ROI remains fixed.

31. The X-ray imaging apparatus according to claim 30, wherein the controller is configured to set the X-ray imaging mode to the stationary mode in response to the movement characteristic of the object of interest being equal to or less than a reference value, and set the X-ray imaging mode to the dynamic mode in response to the movement size of the object of interest being greater than the reference value.

32. The X-ray imaging apparatus according to claim 13, wherein the image processor is configured to combine the current image frame with a pre-generated road map.

33. A method of controlling an X-ray imaging apparatus, the method comprising:
setting an X-ray imaging mode according to a movement characteristic of an object of interest included in an object region;
radiating X-rays onto the object region; and
obtaining image frames of the object region by detecting the radiated X-rays
wherein the X-rays incident on a non-region of interest (ROI) of the object region have a lower dose than a dose of the X-rays incident on an ROI of the object region.

34. The method according to claim 33, wherein the radiating of the X-rays comprises filtering the X-rays incident on the non-ROI.

35. The method according to claim 34, further comprising:
radiating the X-rays onto the ROI in the object region;
detecting the radiated X-rays and obtaining the image frames of the object region based on the detected X-rays; and
setting the ROI using the image frames.

36. The method according to claim 35, wherein the setting the ROI includes detecting an object of interest from a current image frame among the image frames and setting the ROI based on a position, a size, or a movement characteristic of the object of interest.

37. The method according to claim 36, wherein the filtering the X-rays includes moving an ROI filter configured to reduce the radiated X-rays to a position corresponding to a position of the non-ROI based on information about the ROI.

38. The method according to claim 35, further comprising restoring the non-ROI of the image frame by combining a current image frame, obtained when X-rays of the lower dose are incident on the non-ROI, of the image frames, with a previous image frame of the image frames.

39. The method according to claim 38, wherein the restoring the non-ROI includes at least one of averaging the current image frame and the previous image frame, summing the current image frame and the previous image frame, and applying motion-compensated spatial filtering or motion-compensated temporal filtering to the current image frame and the previous image frame.

40. The method according to claim 39, wherein the restoring the non-ROI further includes performing image registration or motion estimation and compensation on the non-ROI that is restored by combining the current frame with the previous image frame.

41. The method according to claim 39, further comprising:
using an image equalization algorithm to match brightness and contrast of the ROI and the non-ROI of the current image frame in which the non-ROI is restored.

42. The method according to claim 33, further comprising:
setting the X-ray imaging mode based on information about the current image frame, information about an imaging mode, or information about a stage of an X-ray imaging operation.

43. The method according to claim 42,
wherein the information about the image frame includes the information on the ROI.

44. The method according to claim 43,
wherein the setting the X-ray imaging mode includes setting the X-ray imaging mode as one of a full imaging mode in which the X-rays of a uniform dose are radiated onto the ROI and the non-ROI and an ROI mode in which the X-rays having the dose lower than the dose of X-rays radiated onto the ROI are radiated onto the non-ROI according to the movement characteristic of the object of interest.

45. The method according to claim 44,
wherein the ROI mode includes a dynamic mode in which the ROI is moved according to a movement of the object of interest or a stationary mode in which a size of the ROI is increased according to the movement of the object of interest and a position of the ROI is fixed.

46. The method according to claim 45,
wherein the setting the X-ray imaging mode includes setting the X-ray imaging mode as the full imaging mode in response to the movement characteristic of the object of interest being greater than a first reference value, and setting the X-ray imaging mode as the ROI mode in response to the movement characteristic of the object of interest being equal to or less than the first reference value.

47. The method according to claim 46,
wherein the setting the X-ray imaging mode includes setting the X-ray imaging mode as the dynamic mode in response to the movement characteristic of the object of interest being equal to or less than the first reference value and greater than a second reference value, and setting the X-ray imaging mode as the stationary mode in response to the movement characteristic of the object of interest being equal to or less than the second reference value.

48. The method according to claim 43,
wherein the setting the X-ray imaging mode includes setting the X-ray imaging mode as one of a dynamic mode in which the ROI is moved according to a movement of the object of interest and a stationary mode in which a size of the ROI is increased according to the movement of the object of interest and a position of the ROI is fixed.

49. The method according to claim 48,
wherein the setting the X-ray imaging mode includes setting the X-ray imaging mode as the stationary mode in response to the movement characteristic of the object of interest being equal to or less than a reference value, and setting the X-ray imaging mode as the dynamic mode in response to the movement characteristic of the object of interest being greater than the reference value.

* * * * *